US008663306B2

(12) United States Patent
Kasprzak et al.

(10) Patent No.: US 8,663,306 B2
(45) Date of Patent: Mar. 4, 2014

(54) INTRODUCER WITH EXTENSION

(75) Inventors: Piotr Miroslaw Kasprzak, Regensberg (DE); David Ernest Hartley, Wannanup (AU); Werner Dieter Ducke, Eight Mile Plains (AU); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/635,573

(22) PCT Filed: Mar. 18, 2011

(86) PCT No.: PCT/US2011/029037
§ 371 (c)(1),
(2), (4) Date: Oct. 16, 2012

(87) PCT Pub. No.: WO2011/116308
PCT Pub. Date: Sep. 22, 2011

(65) Prior Publication Data
US 2013/0030514 A1    Jan. 31, 2013

(30) Foreign Application Priority Data

Mar. 19, 2010 (AU) ................................ 2010201069
Dec. 13, 2010 (AU) ................................ 2010249296

(51) Int. Cl.
*A61F 2/06* (2013.01)
(52) U.S. Cl.
USPC ........................................................ 623/1.12
(58) Field of Classification Search
USPC ................... 623/1.11–1.16, 1.23, 1.35, 1.36;
604/96.01, 264, 523, 104, 164.1,
604/101.01, 101.05, 533; 606/198, 108,
606/194, 195, 191
See application file for complete search history.

(56) References Cited

U.S. PATENT DOCUMENTS

| 5,383,852 | A | * | 1/1995 | Stevens-Wright ......... 604/95.04 |
| 5,746,766 | A | | 5/1998 | Edoga |
| 6,849,087 | B1 | | 2/2005 | Chuter |
| 2002/0143383 | A1 | * | 10/2002 | Parodi ......................... 623/1.11 |

(Continued)

FOREIGN PATENT DOCUMENTS

WO    WO 2010127040    11/2010

OTHER PUBLICATIONS

International Search Report and Written Opinion for PCT/US2011/029037, dated Jul. 21, 2011, 10 pgs.

(Continued)

*Primary Examiner* — Thomas McEvoy
*Assistant Examiner* — Jocelin Tanner
(74) *Attorney, Agent, or Firm* — Brinks Gilson & Lione

(57) ABSTRACT

A stent graft delivery device (1) has an elongated extension piece (20) extending from its proximal end of the introducer portion (3). The elongate extension piece is selectively separable from the introducer portion. A plurality of auxiliary guide wires (50) extend from through the stent graft delivery device and through the elongate extension piece. The auxiliary guide wires can cross over at the proximal end of the extension piece and return. The stent graft delivery device can be introduced into a patient via a femoral artery and the elongated extension piece can extend out an artery of the thoracic arch whereby to extend the auxiliary guide wires out of such an artery to give through and through guide wires. Catheterization of pararenal arteries is then possible via a brachial route.

19 Claims, 21 Drawing Sheets

(56) References Cited

U.S. PATENT DOCUMENTS

| | | | |
|---|---|---|---|
| 2005/0159773 A1* | 7/2005 | Broome et al. | 606/200 |
| 2005/0255317 A1* | 11/2005 | Bavaro et al. | 428/375 |
| 2006/0004433 A1* | 1/2006 | Greenberg et al. | 623/1.11 |
| 2007/0083215 A1 | 4/2007 | Hamer et al. | |
| 2008/0109065 A1* | 5/2008 | Bowe | 623/1.13 |

OTHER PUBLICATIONS

International Preliminary Report on Patentability for PCT/US2011/029037, dated Mar. 22, 2012, 5 pgs.

Response to the International Search Report and Written Opinion, dated Jan. 19, 2012, 11 pgs.

* cited by examiner

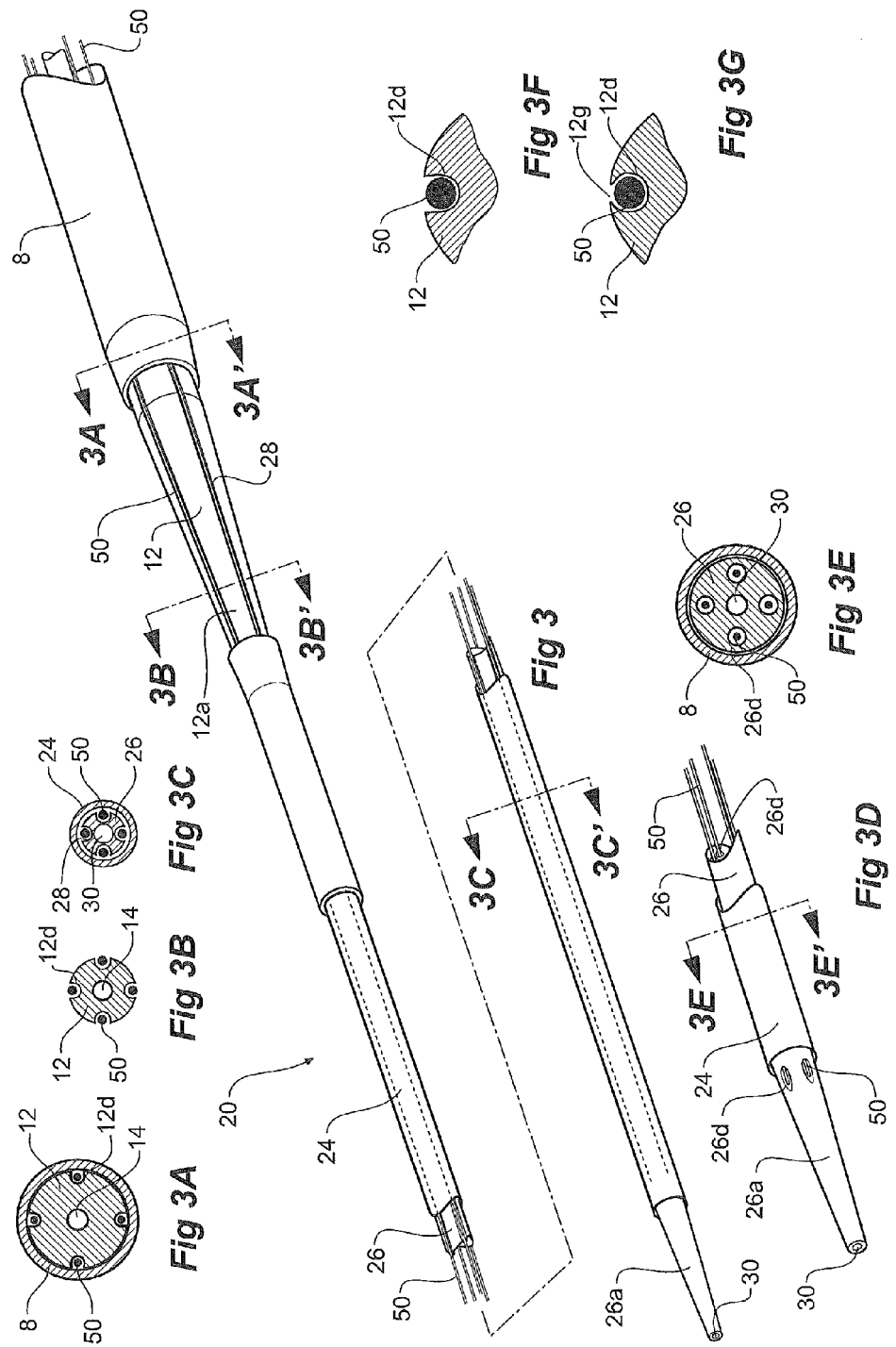

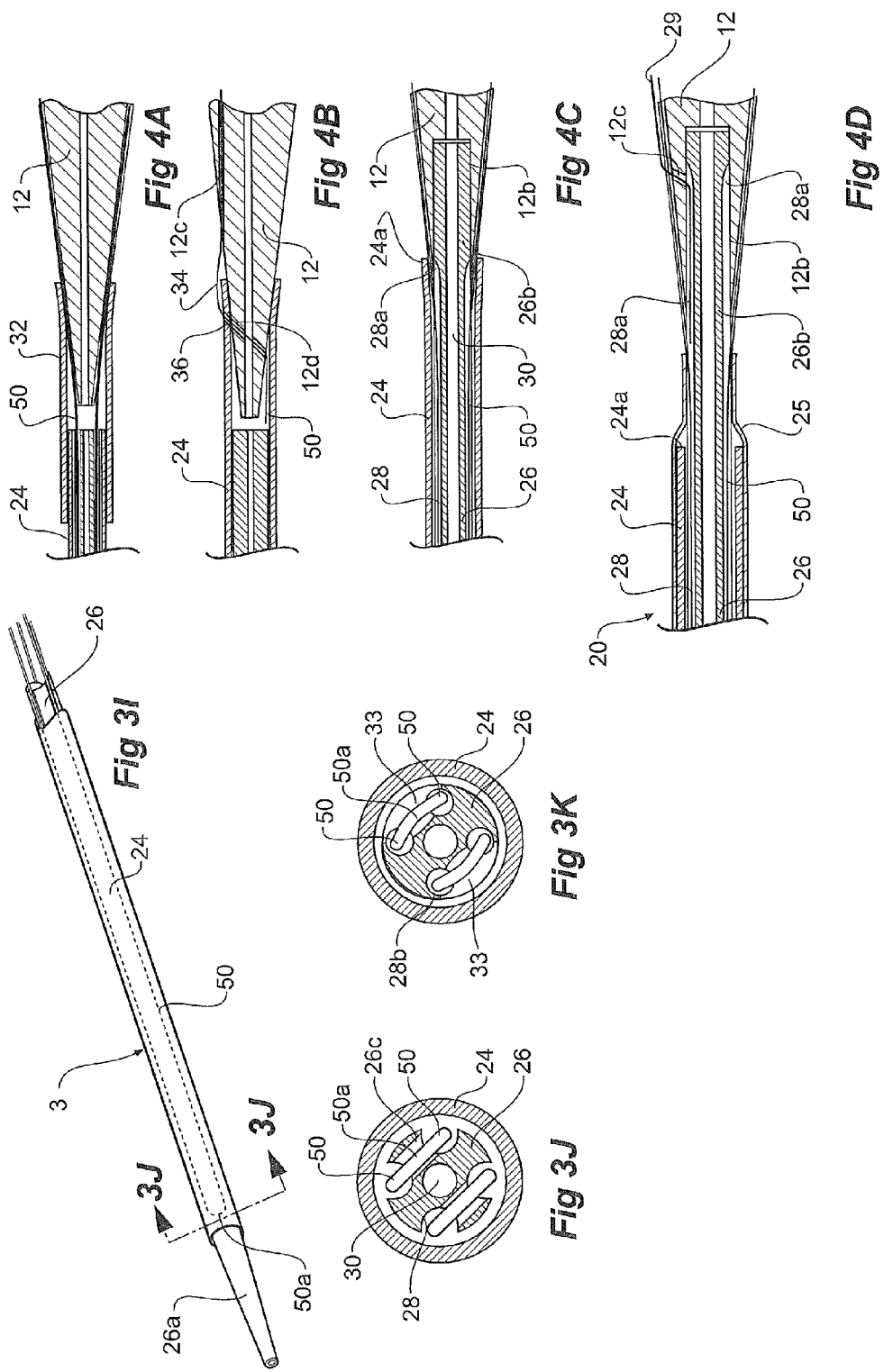

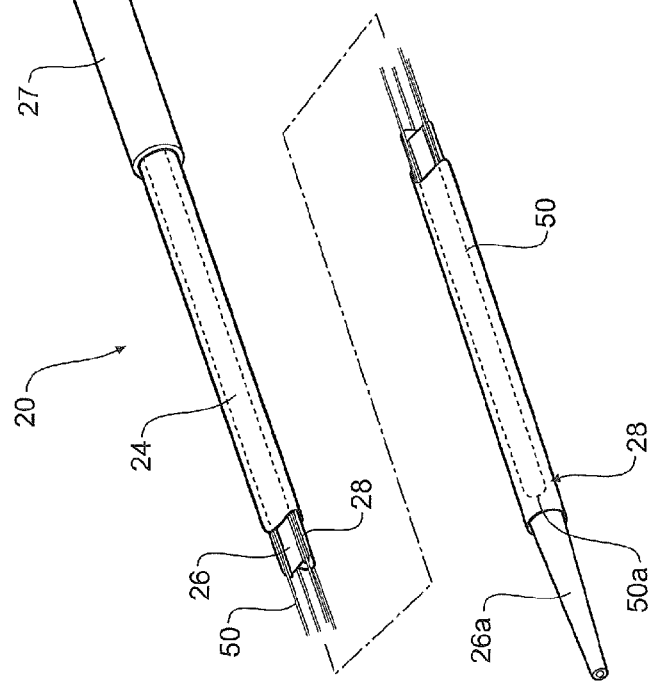
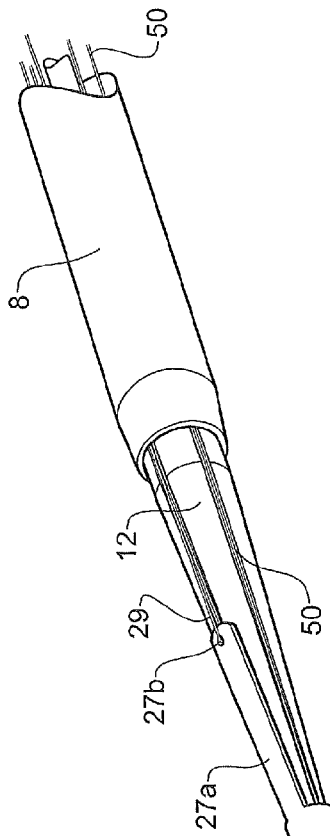
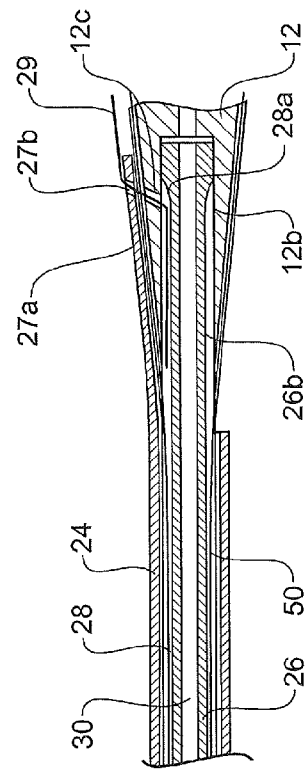
Fig 5A
Fig 5B

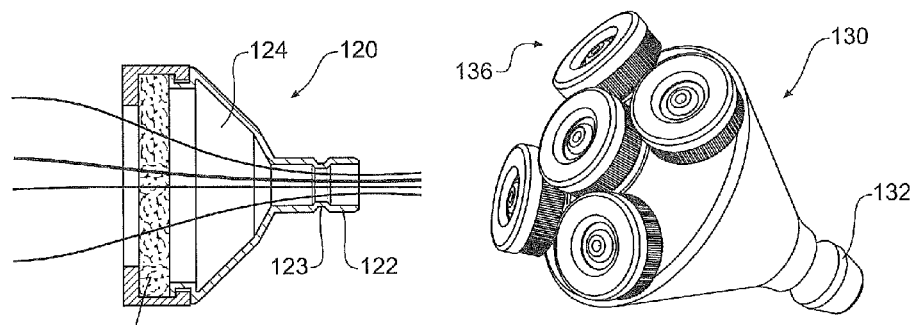
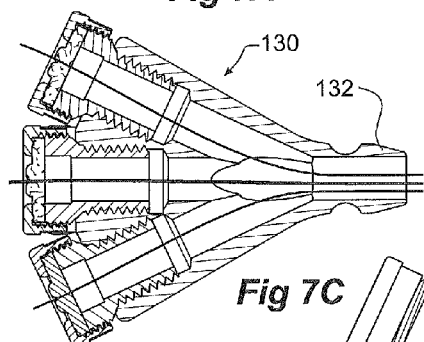
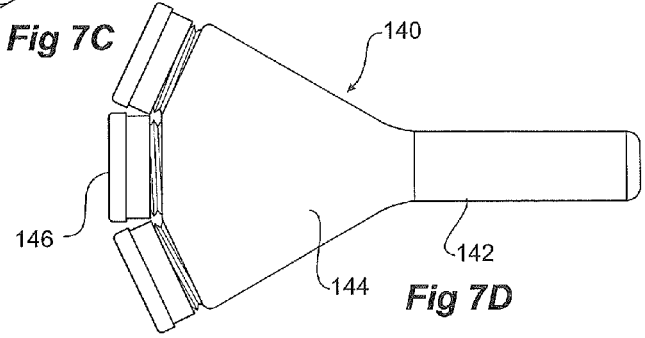
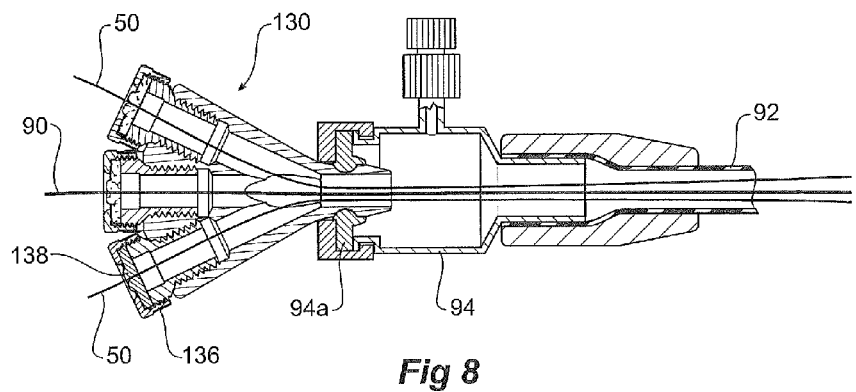

INTRODUCER WITH EXTENSION

RELATED APPLICATIONS

The present application is a §371 filing based on PCT Application Serial No. PCT/US2011/029037, filed Mar. 18, 2011 (and published as WO 2011/116308 on Sep. 22, 2011) designating the United States and published in English, which claims priority to Australian Patent Application Serial No. 2010201069 filed Mar. 19, 2010, and to Australian Patent Application 2010249296 filed Dec. 13, 2010, which foregoing applications are hereby incorporated by reference in their entirety.

TECHNICAL FIELD

This invention relates to a medical device and more particularly to a device for assisting the endovascular deployment of a stent graft into the aorta of a patient.

1. Background Art

A stent graft is used to bridge a defect such as an aneurism in a portion of the vasculature of a patient. The stent graft is introduced in a contracted state through the vasculature by an introduction device and released at a desired location. Where such a portion of the vasculature includes side branch vessels it is necessary to have one or more fenestrations or side arms on the stent graft to enable fluid access to the side branch vessels. Once the stent graft with fenestrations or side arms has been placed in position in the vasculature it is often necessary to catheterize the fenestrations or side arms and deploy extension side arms which extend from the fenestrations or side arms into the branch vessels. Where the stent graft is to be deployed into the portion of the aorta above the renal arteries it can be difficult to catheterize such side arms from a femoral region of the vasculature and hence it may be more desirable to deploy a side branch stent graft from a brachial entry region.

It is an object of this invention to provide a stent graft introduction device which will assist with catheterizing the side arms in such stent grafts.

Throughout this specification the term distal with respect to a portion of the aorta, a deployment device or a prosthesis means the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

2. Disclosure of The Invention

In one form therefore the invention is said to reside in a stent graft delivery device comprising;

an introducer portion, the introducer portion comprising a distal handle portion to remain outside a patient in use and a proximal portion for endovascular introduction into a patient in use, an elongated extension piece extending from the proximal end of the introducer portion, the elongate extension piece being selectively separable from the introducer portion; and a plurality of auxiliary guide wires extending from the introducer portion through the introducer portion and through the elongate extension piece, whereby the stent graft delivery device can be introduced into a patient via a femoral artery and the elongated extension piece can extend out an artery of the thoracic arch whereby to extend the auxiliary guide wires out of such an artery.

It will be seen that by this invention there is provided an arrangement which enables a through and through guide wire set to be introduced into a patient so that relatively easy access can be had to catheterize and deploy side branches into branch vessels such as the renal arteries.

The elongate extension piece is essentially long enough that at least when a stent graft carried on the introduction device is at a desired release position the proximal end of the elongate extension piece extends out through a puncture in the left subclavian artery for instance.

Preferably the elongate extension piece comprises an elongate extension sheath and a extension dilator in the extension sheath and extending proximally thereof, the extension dilator comprising a plurality of longitudinal apertures on an outside surface thereof and the plurality of auxiliary guide wires extending along respective longitudinal apertures.

A stent graft is carried on the introducer portion and preferably the stent graft comprises a tubular body, the tubular body comprising proximal and distal open ends and a plurality of fenestrations or side arms, each of the auxiliary guide wires extending through a respective fenestration or side arm, the auxiliary guide wires extending through the tubular body proximally of the respective fenestration or side arm and outside the tubular body distally of the respective fenestration or side arm.

Preferably the proximal introduction portion comprises a pusher catheter, a guide wire catheter within the pusher catheter, the guide wire catheter being movable with respect to the pusher catheter, a nose cone dilator at the proximal end of the guide wire catheter and the nose cone dilator comprising a plurality of longitudinal grooves on an outside surface thereof to receive respective auxiliary guide wires therealong.

Preferably the plurality of longitudinal grooves on at least part of the outside surface of the nose cone dilator comprise a substantially closed tube except for a narrow elongated opening whereby the respective auxiliary guide wires are received and retained therein.

Preferably the elongate extension piece is removably engaged with the proximal portion by being a friction fit therewith. Alternatively the elongate extension piece is removably engaged with the proximal portion and including a trigger wire release mechanism, whereby upon release of the trigger wire release mechanism the elongate extension piece can be removed from the proximal portion.

Preferably the auxiliary guide wires extend through the introducer portion to the handle portion.

Preferably the auxiliary guide wires include markers at either or both of their proximal or distal ends.

In a preferred embodiment the plurality of auxiliary guide wires comprise a first and a second continuous auxiliary guide wire, each continuous wire extending from the distal handle portion to the proximal end of the elongate extension piece and returning to the distal handle portion.

In one arrangement the elongate extension piece comprises an elongate extension sheath and an extension dilator in the extension sheath and the extension dilator extending proximally of extension sheath, the extension dilator comprising a plurality of longitudinal apertures and the auxiliary guide wires extending through the longitudinal apertures, a pair of scallops extending into the extension dilator at the proximal end of the extension dilator between adjacent longitudinal apertures whereby the auxiliary wires cross over to return in an adjacent longitudinal aperture. Alternatively the extension dilator comprising a plurality of longitudinal grooves on an outside surface thereof and the plurality of auxiliary guide wires extending along respective longitudinal grooves, a pair of cross apertures extending into the extension dilator between adjacent longitudinal grooves at the proximal end of the extension dilator whereby each of the auxiliary guide wires cross through a respective cross aperture to return in an adjacent longitudinal groove.

In an alternative form the invention comprises a stent graft delivery device and stent graft in combination, the stent graft being loaded onto the delivery device;

the delivery device comprising an introducer portion and an elongated extension piece extending from the proximal end of the introducer portion, the introducer portion comprising a distal handle portion to remain outside a patient in use and a proximal portion for endovascular introduction into a patient, the elongate extension piece selectively separable from the introducer portion and a plurality of auxiliary guide wires extending from the distal end of the introducer portion through the introducer portion and through the elongate extension piece to a proximal end of the elongate extension piece, the elongate extension piece comprising an elongate extension sheath and a extension dilator in the extension sheath and extending proximally thereof, the extension dilator comprising a plurality of longitudinal grooves on an outside surface thereof;

the introduction portion comprising a pusher catheter, a guide wire catheter within the pusher catheter, the guide wire catheter being movable with respect to the pusher catheter, a nose cone dilator at the proximal end of the guide wire catheter and the nose cone dilator comprising a plurality of longitudinal grooves on an outside surface thereof.

the stent graft comprising a tubular body, the tubular body comprising proximal and distal open ends and a plurality of fenestrations or side arms, the stent graft being retained on the introduction portion distally of the nose cone dilator and proximally pusher catheter;

each of the auxiliary guide wires extending through a respective fenestration or side arm, the auxiliary guide wires extending through the tubular body proximally of the respective fenestration or side arm and outside the tubular body distally of the respective fenestration or side arm;

whereby the stent graft delivery device can be introduced into a patient via a femoral artery and the elongate extension piece can extend out a thoracic arch artery whereby to extend the auxiliary guide wires out of such an artery and the respective auxiliary guide wires can be used to catheterize the respective fenestration or side arm and subsequently to deploy an extension stent graft therethrough.

In an alternative form the invention comprises a stent graft delivery device and stent graft in combination, the stent graft being loaded onto the delivery device;

the delivery device comprising an introducer portion and an elongate extension piece extending from the proximal end of the introducer portion, the introducer portion comprising a distal handle portion to remain outside a patient in use and a proximal introduction portion for endovascular introduction into a patient;

the proximal introduction portion comprising a pusher catheter, a guide wire catheter within the pusher catheter, the guide wire catheter being movable with respect to the pusher catheter, a nose cone dilator at the proximal end of the guide wire catheter, the nose cone dilator comprising a plurality of longitudinal grooves on an outside surface thereof;

the elongate extension piece comprising an extension sheath and a extension dilator in the extension sheath and extending proximally thereof, the extension dilator comprising a plurality of longitudinal grooves on an outside surface thereof;

the extension sheath being engaged with a proximal end of the nose cone dilator and being selectively separable from the nose cone dilator;

a plurality of auxiliary guide wires extending from the distal end of the introducer portion through the pusher catheter, along the longitudinal grooves in the nose cone dilator, into and through the extension sheath in the longitudinal grooves on the extension dilator;

the plurality of auxiliary guide wires comprising a first and a second continuous wire, each continuous wire extending from the distal handle portion to the proximal end of the elongate extension piece and returning to the distal handle portion;

the elongate extension piece comprising an elongate extension sheath and an extension dilator in the extension sheath and the extension dilator extending proximally of extension sheath, the extension dilator comprising a plurality of longitudinal apertures and the auxiliary guide wires extending through the longitudinal apertures, a pair of scallops extending into the extension dilator at the proximal end of the extension dilator between adjacent longitudinal apertures whereby the auxiliary wires cross over to return in an adjacent longitudinal aperture;

the stent graft comprising a tubular body, the tubular body comprising proximal and distal open ends and a plurality of fenestrations;

each of the auxiliary guide wires extending through a respective fenestration, the auxiliary guide wires extending through the tubular body proximally of the respective fenestration and outside the tubular body distally of the respective fenestration;

whereby the stent graft delivery device can be introduced into a patient via a femoral artery and the elongated dilator extension can extend out of a thoracic arch artery whereby to extend the auxiliary guide wires out of the artery and subsequently to cut the first and the second continuous wire where they extend out through the artery to give four auxiliary guide wires and then to deploy side arm extension along the respective guide wires into the respective fenestrations.

In an alternative form the invention comprises a manifold adaptor piece comprising a spigot to engage into the haemostatic seal of an endovascular port hub, a substantially funnel shaped body extending from the spigot and at least one port, the at least one port comprising a seal disc.

In a preferred embodiment the manifold adaptor piece comprises five individual ports, each port comprising a sealing disc.

The manifold adaptor piece can be used with the stent graft delivery device of the present invention to provide a access port at the exit point from the left subclavian artery so that the auxiliary guide wires can be trained through the or respective ports to assist deployment of side branch stent grafts therethrough. The manifold adaptor piece can assist with preventing the various auxiliary guide wire from becoming entangled with each other.

BRIEF DESCRIPTION OF THE DRAWINGS

FIG. 3 shows detail of a portion of the delivery device shown in FIG. 1;

FIGS. 3A to 3C show cross sectional views of portions of the delivery device according to the present invention;

FIG. 3D shows an alternative embodiment of dilator tip on the extension piece;

FIG. 3E shows a cross sectional view of the extension piece of FIG. 3D;

FIG. 3F shows detail of an alternative embodiment of a longitudinal groove in the nose cone dilator;

FIG. 3G shows detail of one embodiment of a longitudinal groove in the nose cone dilator;

FIG. 3I shows an alternative embodiment of extension piece;

FIGS. 3J and 3K show an alternative arrangements of the return auxiliary guide wires in the extension piece;

FIGS. 4A to 4D show longitudinal section views of alternative connection arrangements between the nose cone dilator and the elongate extension piece;

FIG. 5A shows an alternative embodiment of extension piece;

FIG. 5B shows a longitudinal section view of the connection arrangements between the nose cone dilator and the elongate extension piece of FIG. 5A;

FIGS. 7A to 7D show alternative embodiments of a manifold adaptor piece for use with the present invention; and FIG. 8 shows the use of the manifold adaptor piece shown in FIGS. 7B and 7C.

DESCRIPTION OF PREFERRED EMBODIMENTS

Figure 1A:
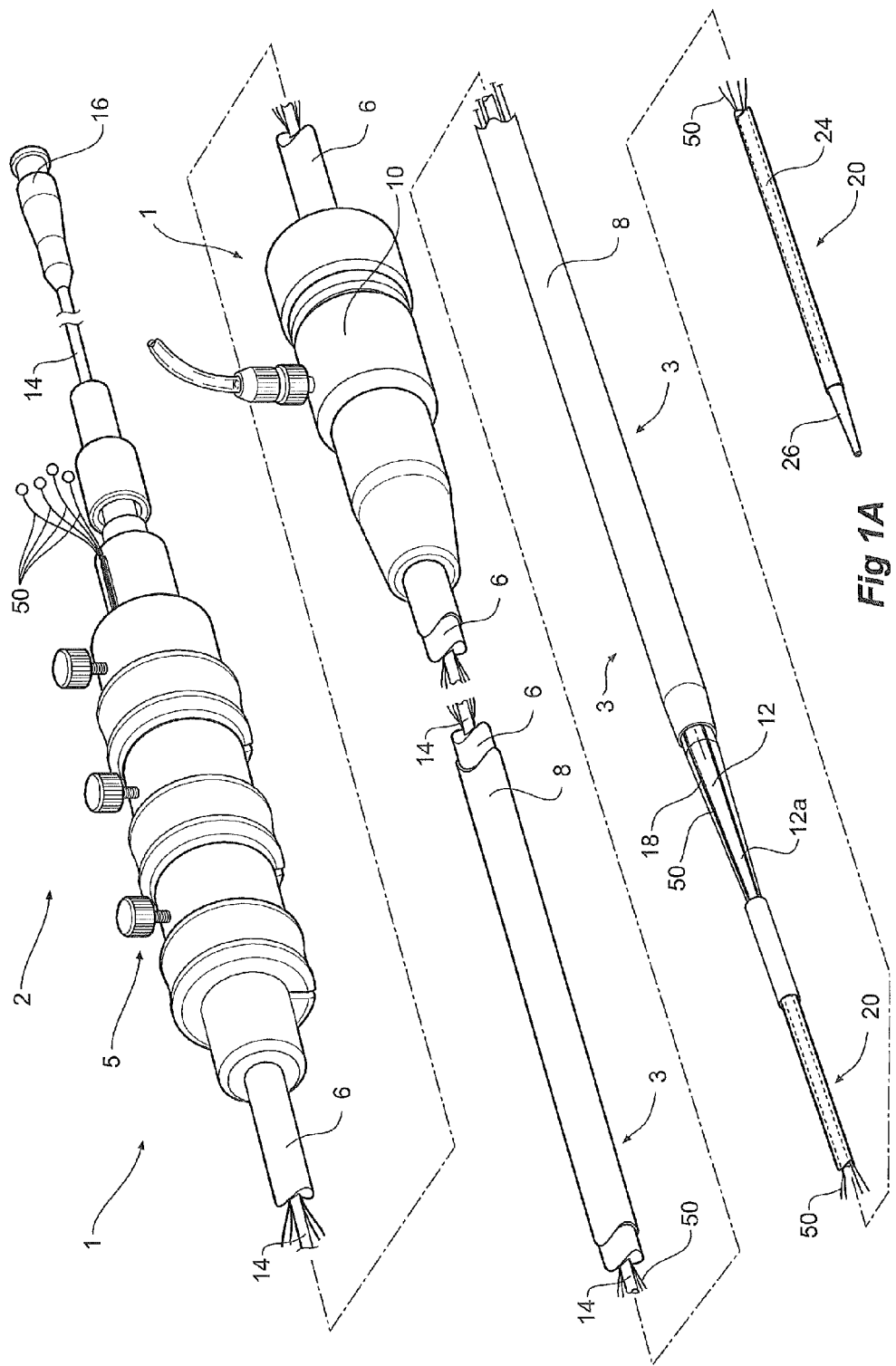
FIGS. 1A and 1B show a stent graft delivery advice according to one embodiment of the present invention.
Figure 1B:
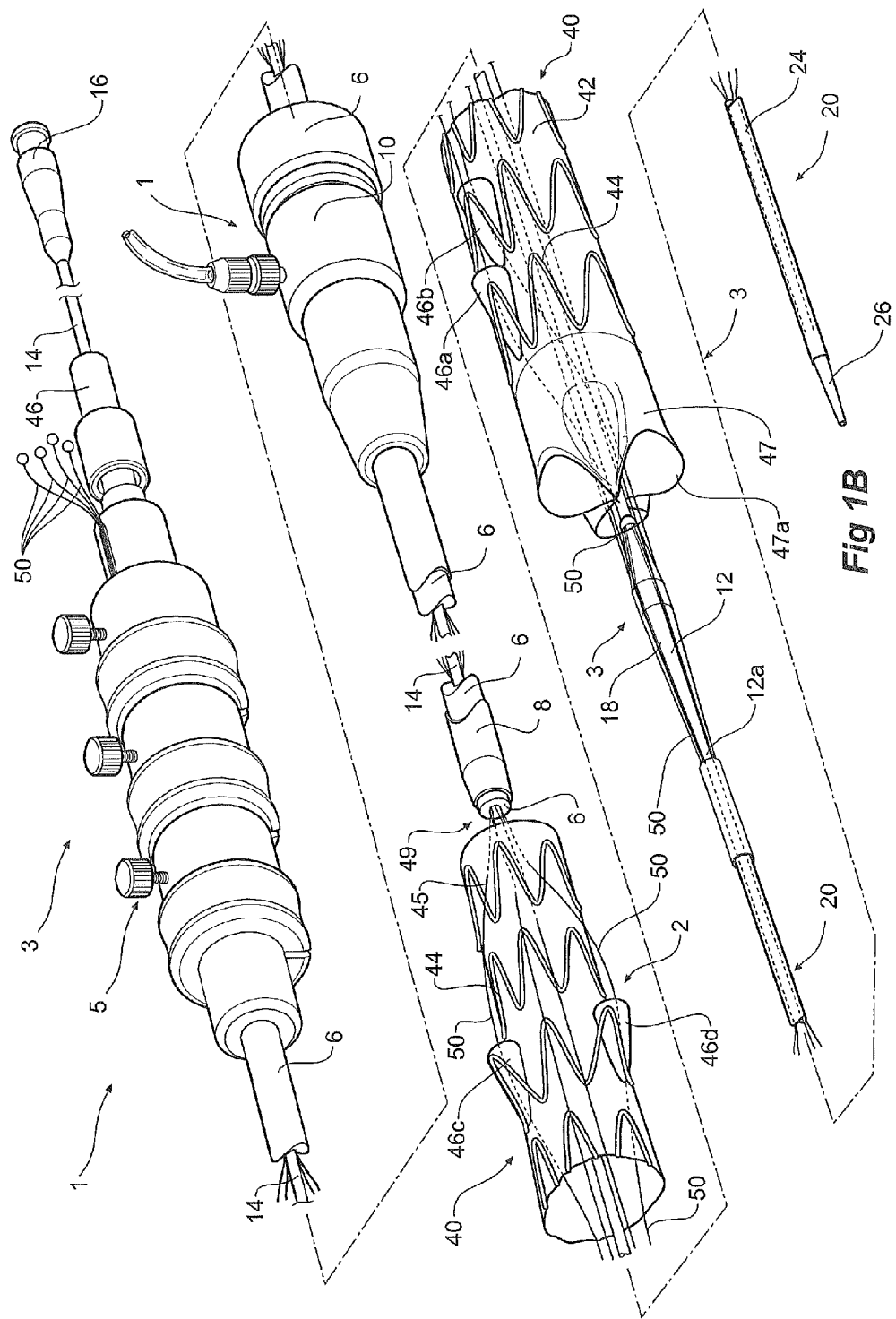

Now looking at the drawings in more detail and in particular FIGS. 1A and 1B in which a stent graft deployment device of one embodiment of the present invention is shown.

FIG. 1A shows the stent graft delivery device in a condition for introduction into a patient and FIG. 1B shows the device of FIG. 1A with the sheath withdrawn to show the stent graft. The particular configuration shown in FIG. 1B would not actually occur in use, because, by the time that the sheath has been withdrawn to expose the stent graft the extension piece would have been withdrawn as is discussed below.

The delivery device 1 comprises a handle portion 2 and an introduction portion 3. The handle portion is intended to remain outside a patient in use and the introduction portion is intended to be introduced into a patient via a puncture into a artery such as the femoral artery. A pusher catheter 6 extends proximally from a trigger wire release region 5 of the handle 2. A sheath 8 and sheath hub 10 extends over the pusher catheter 6. The sheath 8 extends proximally to a nose cone dilator 12. The sheath can be retracted to expose a stent graft retained below it as is discussed below. A guide wire cannula 14 extends from a Luer lock hub 16 at the distal end of the device through the handle and pusher catheter to extend to and through the nose cone dilator 12. The Luer lock hub 16 is used to introduce liquids such as contrast media to enable tracking of the progress of an operation.

The nose cone dilator 12 has a plurality of longitudinal grooves 18 on its outside longitudinal surface. The grooves are shown in detail in FIGS. 3A, 3B, 3F and 3G. Into these grooves 18 lie auxiliary guide wires 50 as will be discussed below in more detail.

An elongate extension piece 20 is releasably mounted to the proximal end 12a of the nose cone dilator 12. The releasable mounting may be achieved by a friction fit between the tapered tip 12a of the nose cone dilator 12 as is shown in FIG. 4A or it may be by a trigger wire system as is shown and discussed in relation to FIG. 4B. Other methods of releasably retaining the elongate extension piece 20 to the proximal end 12a of the nose cone dilator 12 are also within the scope of the invention and are shown in FIGS. 4C and 4D and 5A and 5B and are discussed in more detail below.

As can be seen in FIG. 1B a stent graft 40 is releasably retained on the introduction device 1 at the proximal end thereof and distal of the nose cone dilator. The stent graft is retained in a compressed condition under the sheath 8 just distal of the nose cone dilator by releasable trigger wires (not shown) and when the sheath is withdrawn the stent graft expands to the configuration shown in FIG. 1B. In this configuration the proximal end 47 of the stent 40 is retained to the introducer device at a point just distal of the nose cone dilator 12 but access through the open lobes of graft material 47a can be achieved to track an access catheter over the auxiliary guide wires as is discussed below.

Figure 2:
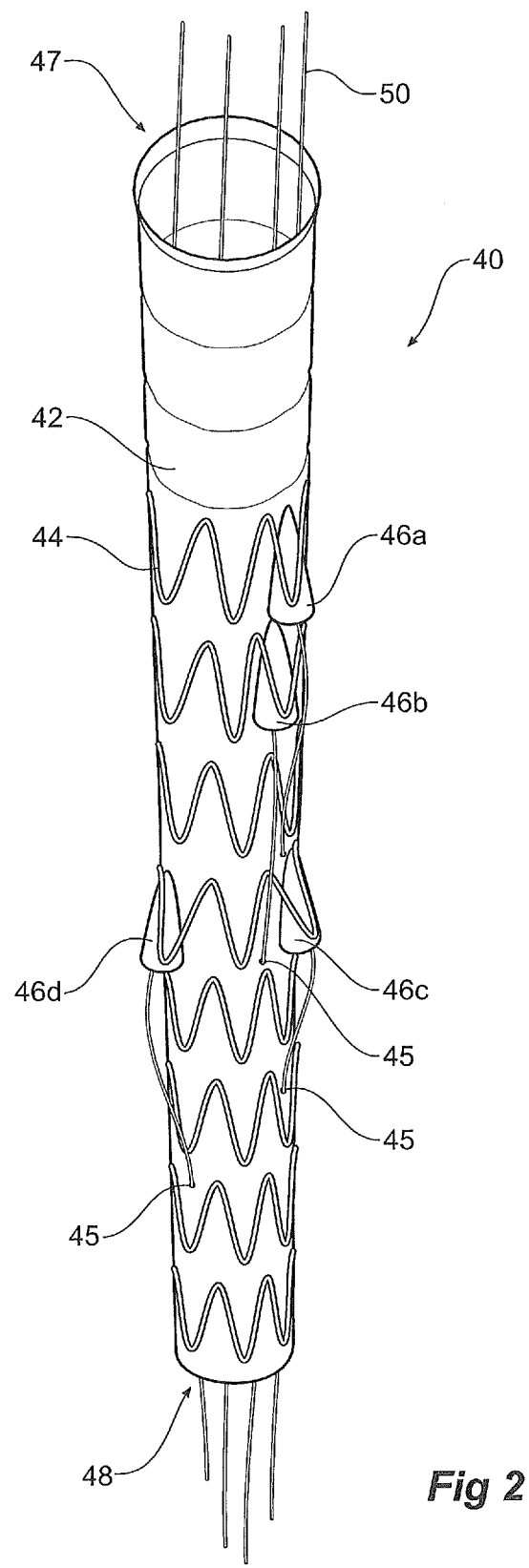
FIG. 2 shows a stent graft suitable for the present invention with pre-loaded guide wires.

FIG. 2 shows a stent graft suitable for use with the present invention. The stent graft as shown in FIG. 2 has a tubular body of a biocompatible graft material which is supported by self expanding zig zag stents. The stent graft has a number of low profile side arms each of which open outside the stent graft facing distally. These side arms are for receiving side arm extensions to extend to the side branch arteries in the region of the renal arteries. The side branch arteries in the region of the renal arteries are the left and right arteries and the superior mesenteric and the celiac arteries. As an alternative to low profile side arms there may be fenestrations or other forms of aperture in the sent graft wall.

The stent graft 40 has a tubular body 42 of a biocompatible graft material which is supported by self expanding zig zag stents 44. The stent graft 40 has a number of low profile side arms 46a, 46b, 46c and 46d each of which open outside the stent graft facing distally. Four auxiliary guide wires 50 extend through the stent graft from a proximal end 47 and out through the low profile side arms 46a, 46b, 46c and 46d respectively and extend outside of the stent graft distally of the respective low profile side arms 46a, 46b, 46c and 46d. At some distance before the distal end 48 of the stent graft they extend into the interior of the stent graft through the biocompatible material wall and continue on distally. As can be seen in FIG. 1A the auxiliary guide wires 50 extend into the lumen 49 of the pusher catheter 6 and exit at the distal end of the handle 5. Each of the auxiliary guide wires 50 can have a marker tag connected to the wire where it exits from the distal end of the handle 5 so that a physician knows which wire extends through which side arm or fenestration.

As can be seen in detail in FIG. 3 the elongate extension piece 20 comprises an outer sheath 24 and a dilator 26. The dilator has a plurality of longitudinal groves 28 on its outside surface in it as can also be seen in the cross section shown in FIG. 3C which shows a cross section of the elongate extension piece along the line 3C-3C' in FIG. 3. Into these grooves 28 lie the auxiliary guide wires 50 as will be discussed below in more detail. The elongate extension piece 20 also has a guide wire lumen 30. The auxiliary guide wires 50 extend within the sheath 24 in the longitudinal grooves 28 nearly to the proximal end 26a of the dilator 26.

FIG. 3A shows a cross section along the line 3A-3A' on the nose cone dilator 12 of FIG. 3. The nose cone dilator 12 is surrounded by the sheath 8 and has four longitudinal grooves 12d arranged orthogonally on its outer surface. Into each of these grooves is received an auxiliary guide wire 50. A detail of such a groove is shown in FIG. 3F.

FIG. 3B shows a cross section along the line 3B-3B' on the tapered region nose cone dilator 12 of FIG. 3. The tapered region of the nose cone dilator 12 has four longitudinal grooves 12d arranged orthogonally on its outer surface. Into each of these grooves is received an auxiliary guide wire 50. A detail of such a groove is shown in FIG. 3F.

As an alternative the grooves in the tapered region may be a shown in FIG. 3G. In this embodiment the grooves 12f are a substantially closed tube except for a narrow elongated opening 12g whereby the respective auxiliary guide wires are received and retained therein. Preferably the substantially closed portion of the grooves 12f is on the tapered portion of the nose cone dilator. With the guide wires retained in the substantially closed groove there is less chance of the wire coming out of the groove during deployment and possible causing trouble entangling with other portions of the delivery device. The nose cone dilator is formed from a polyurethane material which exhibits a degree of elasticity or flexibility so that when it is desired to remove the auxiliary guide wire the sided of the opening can be deflected to allow removal. During use of the delivery device of the present invention as discussed in more detail below a sheath and dilator are fed down over the auxiliary guide wire from the proximal end and the dilator acts to draw the auxiliary guide wire out of the substantially closed groove.

FIGS. 3D and 3E show a portion of the proximal end of an extension piece and a transverse cross sectional view of a proximal end of the extension piece showing an alternative embodiment according to the present invention. In this embodiment the same reference numerals are used for corresponding items to those shown in FIGS. 3 to 3C. In this embodiment instead of grooves in the outer surface of the extension dilator 26 there are four longitudinal apertures 26d into which the auxiliary wires 50 are received to extend from the distal end of the extension dilator to the proximal end 26a.

FIGS. 3I and 3K show an alternative embodiment of a portion of the proximal end of an extension piece and a transverse cross sectional view of a proximal end of the extension piece 20. In this embodiment the same reference numerals are used for corresponding items to those shown in FIGS. 3 to 3C. In this embodiment instead of grooves in the outer surface of the extension dilator 26 there are four longitudinal apertures 28b into which the auxiliary wires 50 are received to extend from the distal end 26b of the extension dilator to the proximal end 26a. At the proximal end 26a of the extension dilator 26 a scallop 33 is cut into the extension dilator to expose two adjacent longitudinal apertures 28b so that the auxiliary wire 50 and cross over at 50a to extend back down the adjacent longitudinal groove 28b.

FIG. 3K shows an alternative embodiment of a portion of the proximal end of an extension piece in a transverse cross sectional view. In this embodiment the auxiliary guide wires 50 comprised first and second auxiliary guide wires which extend from the distal end of the delivery device and cross over and return to the distal end of the delivery device. The first and second auxiliary guide wires extend along longitudinal grooves 28 on the outside surface of the dilator 26 of the extension piece 3 and then there are a pair of cross apertures 26c extending into the extension dilator between adjacent longitudinal grooves 28 at the proximal end of the extension dilator whereby each of the auxiliary guide wires cross through a respective cross aperture to return in an adjacent longitudinal groove.

A friction fit between the tapered tip 12a of the dilator 12 and the elongate extension piece 24 as is shown in FIG. 4A may be achieved by a flexible sleeve 32 which is affixed to the outer sheath 24 of the elongate extension piece and extends distally of the outer sheath 24 and which engages with the proximal end 12a of the nose cone dilator 12 and is retained there by friction. When the elongate extension piece is to be removed from the nose cone dilator, as is discussed below, a sharp pull on the elongate extension piece from its proximal end would be sufficient to release it from the nose cone dilator.

An alternative arrangement for the retention of the elongate extension piece on the nose cone dilator is shown in FIG. 4B and comprises a trigger wire system between the tapered tip 12a of the dilator 12 and the elongate extension piece 24 as is shown in FIG. 4B. A trigger wire 34 extends out of an elongate aperture 12c in the nose cone dilator and through an aperture 36 in the outer sleeve 24 of the elongate extension piece 20 and back onto the nose cone dilator through aperture 12d and thereby retains the outer sleeve to the nose cone dilator. The trigger wire 34 can extend to a trigger wire release mechanism 5 on the handle 2 of the introducer device 1. When the trigger wire is withdrawn by activation of the trigger wire release mechanism 5 during a deployment procedure the sleeve 24 can be removed from the nose cone dilator.

FIG. 4C shows a still further arrangement for the connection arrangement between the nose cone dilator and the elongate extension piece. In this embodiment the same reference numerals are used for corresponding items to those shown in FIGS. 3 to 3C. As can be seen in detail in FIG. 4C the elongate extension piece 20 comprises an outer sheath 24 and a dilator 26. The dilator has a plurality of longitudinal groves 28 on its outside surface. Into these grooves 28 lie the auxiliary guide wires 50. The elongate extension piece 20 also has a guide wire lumen 30. The longitudinal grooves 28 terminate at 28a before the distal end 26b of the dilator 26. The distal end 26b of the extension dilator 26 fits into the proximal recess 12b in the nose cone dilator 12. The extension sleeve 24 has a slightly flared distal end 24a to fit over the proximal end of the nose cone dilator 12.

Hence, in this embodiment the distal end 26b of the extension dilator 26 fits into and is retained in proximal recess 12b in the nose cone dilator 12 by a combination of factors. First the push fit of the distal end 26b of the extension dilator 26 in the proximal recess 12b provides a degree of retention. Second, the auxiliary guide wires can be locked at the handle portion and with the bend at 50a the extension piece cannot move forward and thereby holds the distal end 26b of the dilator 26 in the recess 12b.

FIG. 4D shows a still further arrangement for the connection arrangement between the nose cone dilator and the elongate extension piece. In this embodiment the same reference numerals are used for corresponding items to those shown in FIGS. 3 to 3C. As can be seen in detail in FIG. 4D the elongate extension piece 20 comprises an outer sheath 24 and a dilator 26. The dilator has a plurality of longitudinal groves 28 on its outside surface. Into these grooves 28 lie the auxiliary guide wires 50. The elongate extension piece 20 also has a guide wire lumen 30. The longitudinal grooves 28 terminate at 28a before the distal end 26b of the dilator 26. The distal end 26b of the extension dilator 26 fits into the proximal recess 12b in the nose cone dilator 12. At the distal end of the outer sheath a sleeve 25 is shrink fitted and/or glued onto the outer sheath and distal of the distal end 24a of the sheath 24 the sleeve 25 is shrunk to the size of the dilator to hold the auxiliary wires into their respective grooves in the dilator. In this embodiment a hole 12c extends through the nose cone dilator and opens into proximal recess 12b in the nose cone dilator 12. A trigger wire 29 which extends from the handle of the delivery device enters the hole 12c and then into the longitudinal groove 28 just proximal of the end 28a of the groove 28 as can be seen in FIG. 3G.

Hence, in this embodiment the distal end 26b of the extension dilator 26 fits into and is retained in proximal recess 12b in the nose cone dilator 12 by a combination of factors. First the push fit of the distal end 26b of the extension dilator 26 in the proximal recess 12b provides a degree of retention. Second, the terminating recesses 28a means that if the dilator 26 is pulled independently of the sheath 24 the trigger wire 29 in the grooves 28 interferes and prevents the removal. Third, the auxiliary guide wires can be locked at the handle portion and with the bend at 50*a* the extension piece cannot move forward and thereby holds the distal end 26*b* of the dilator 26 in the recess 12*b*.

FIGS. 5A and 5B show an alternative arrangement for the connection arrangement between the nose cone dilator and the elongate extension piece. In this embodiment the same reference numerals are used for corresponding items to those shown in FIGS. 3 to 3C.

As can be seen in detail in FIG. 5A the elongate extension piece 20 comprises an outer sheath 24 and a dilator 26. The dilator has a plurality of longitudinal groves 28 on its outside surface. Into these grooves 28 lie the auxiliary guide wires 50. The elongate extension piece 20 also has a guide wire lumen 30. The longitudinal grooves 28 terminate at 28*a* before the distal end 26*b* of the dilator 26. The distal end 26*b* of the extension dilator 26 fits into the proximal recess 12*b* in the nose cone dilator 12. At the distal end of the outer sheath a sleeve 27 is shrink fitted and/or glued onto the outer sheath and includes an elongate tab 27*a* which extends distally along the nose cone dilator 12 when the distal end of the dilator is received into the proximal recess 12*b* in the nose cone dilator 12. At the end of the elongate tab 27*a* is a hole 27*b*. A corresponding hole 12*c* extends through the nose cone dilator and opens into proximal recess 12*b* in the nose cone dilator 12. A trigger wire 29 which extends from the handle of the delivery device enters the hole 27*b* and then the hole 12*c* and then into the longitudinal groove 28 just proximal of the end 28*a* of the groove 28 as can be see in FIG. 5B.

Hence the distal end 26*b* of the extension dilator 26 fits into and is retained in proximal recess 12*b* in the nose cone dilator 12 by a combination of factors. First the push fit of the distal end 26*b* of the extension dilator 26 in the proximal recess 12*b* provides a degree of retention. Second, the terminating recesses 28*a* mean that if the dilator 26 is pulled independently of the sheath 24 the trigger wire 29 in the grooves 28 interferes and prevent the removal. Third, the trigger wire engaged into the aperture 12*c* prevents the sleeve 27 which is shrink fitted and/or glued onto the sheath being pulled distally until the trigger wire has been removed. Fourthly, the auxiliary guide wires can be locked at the handle portion and with the bend at 50*a* the extension piece cannot move forward and thereby holds the distal end 26*b* of the dilator 26 in the recess 12*b*.

Figure 6A:
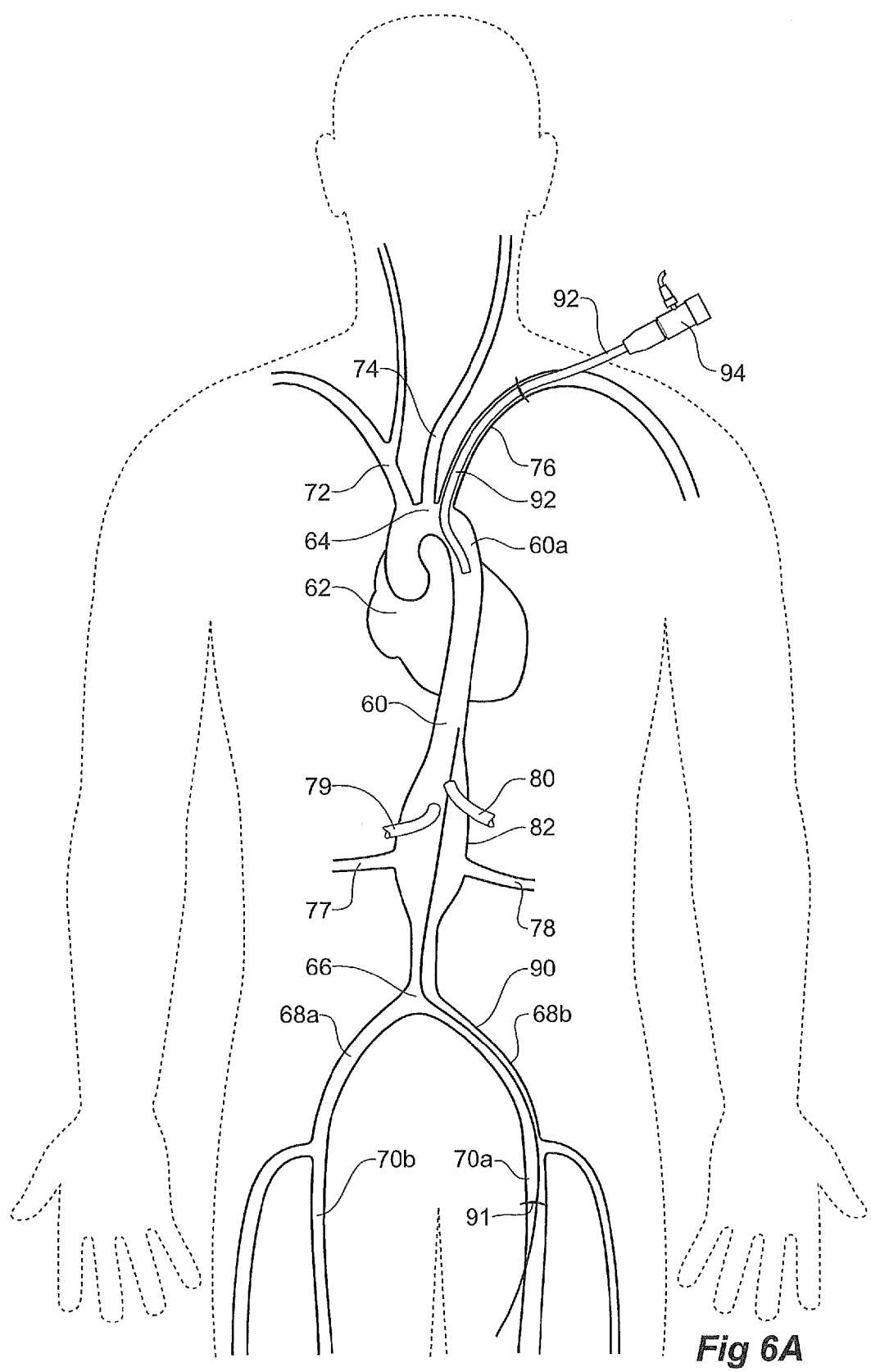
FIGS. 6A to 6N show various stages in the deployment of a stent graft using a delivery device according to the present invention.
Figure 6B:
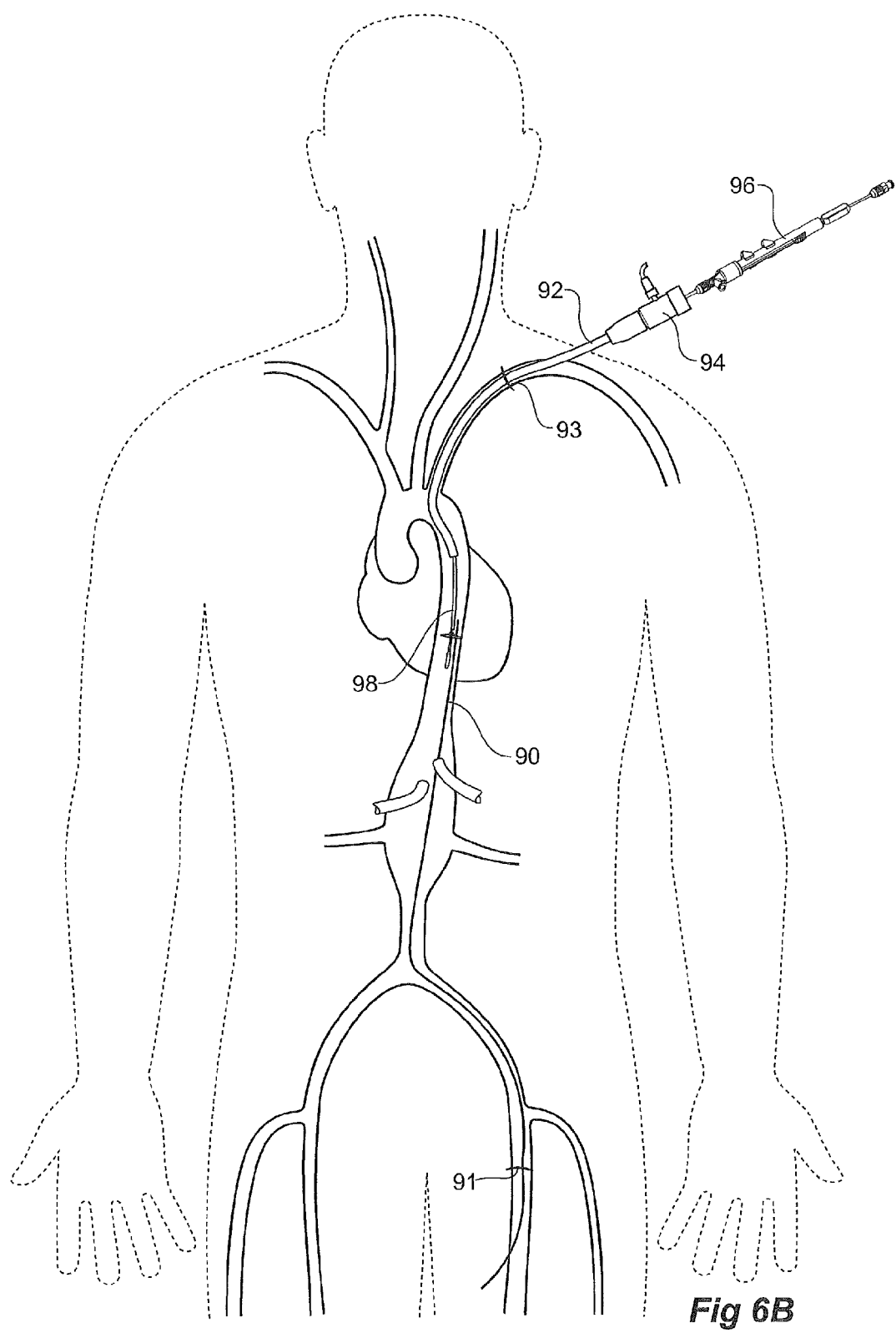
Figure 6C:
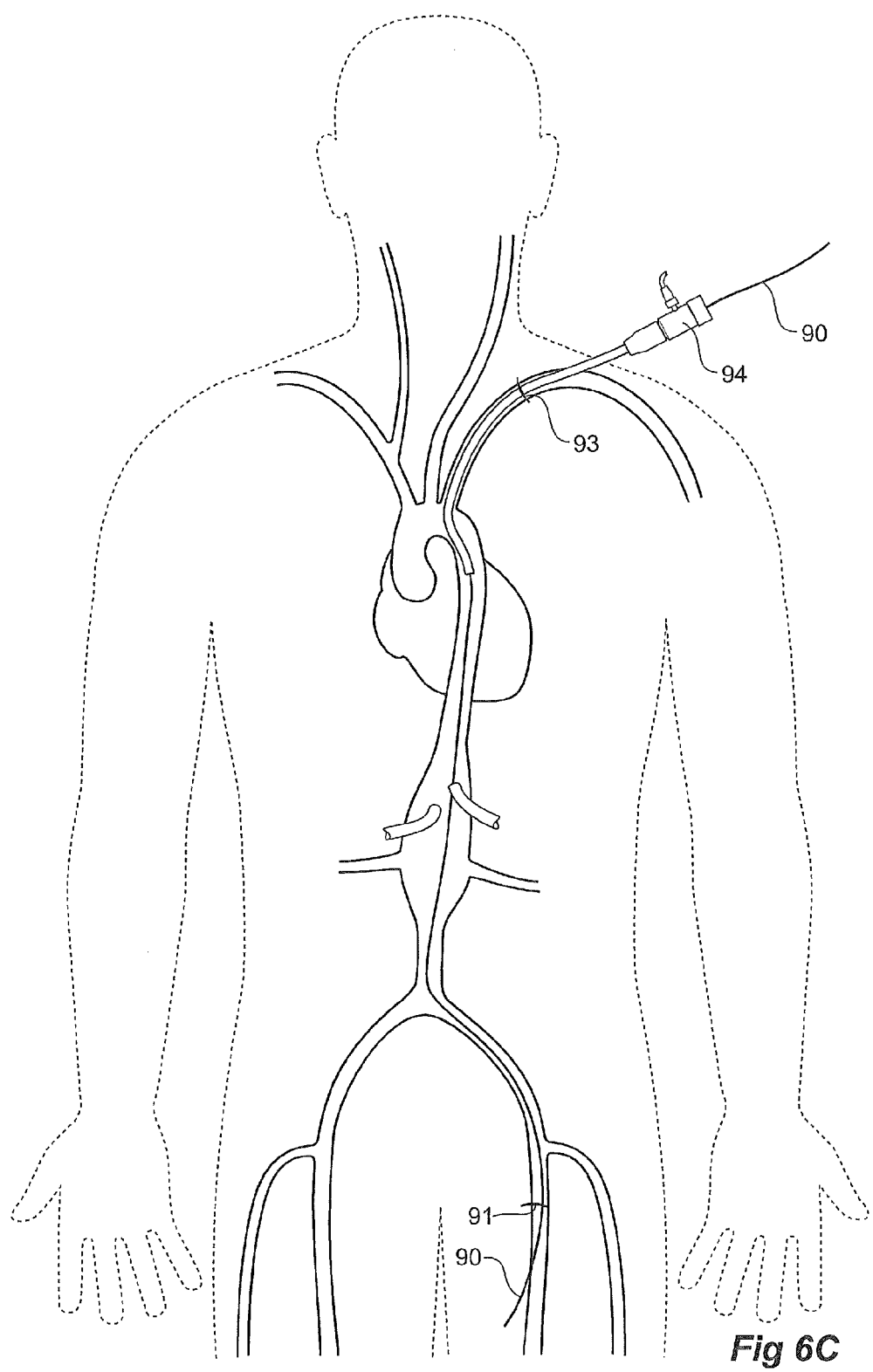
Figure 6D:
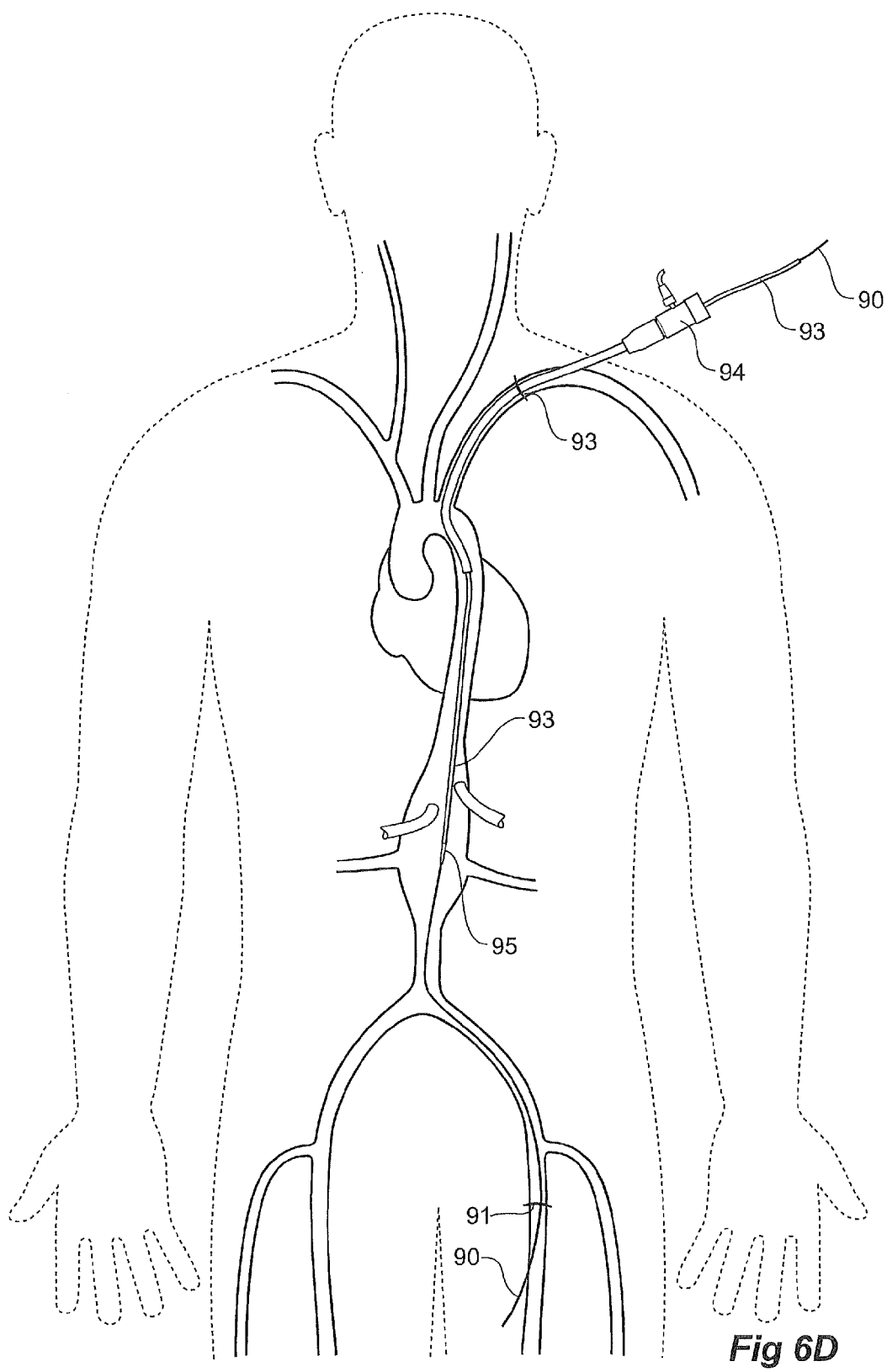
Figure 6E:
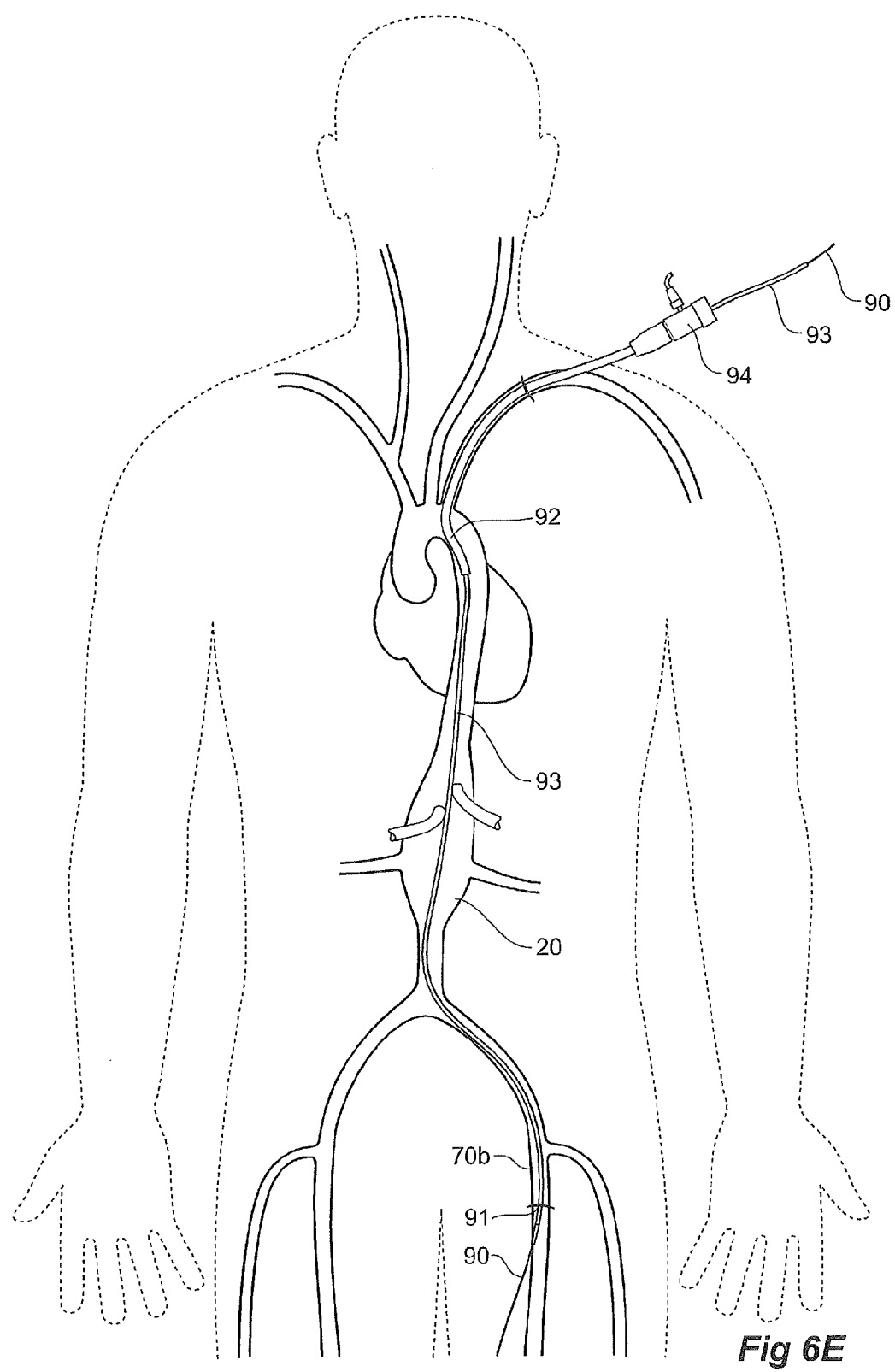
Figure 6F:
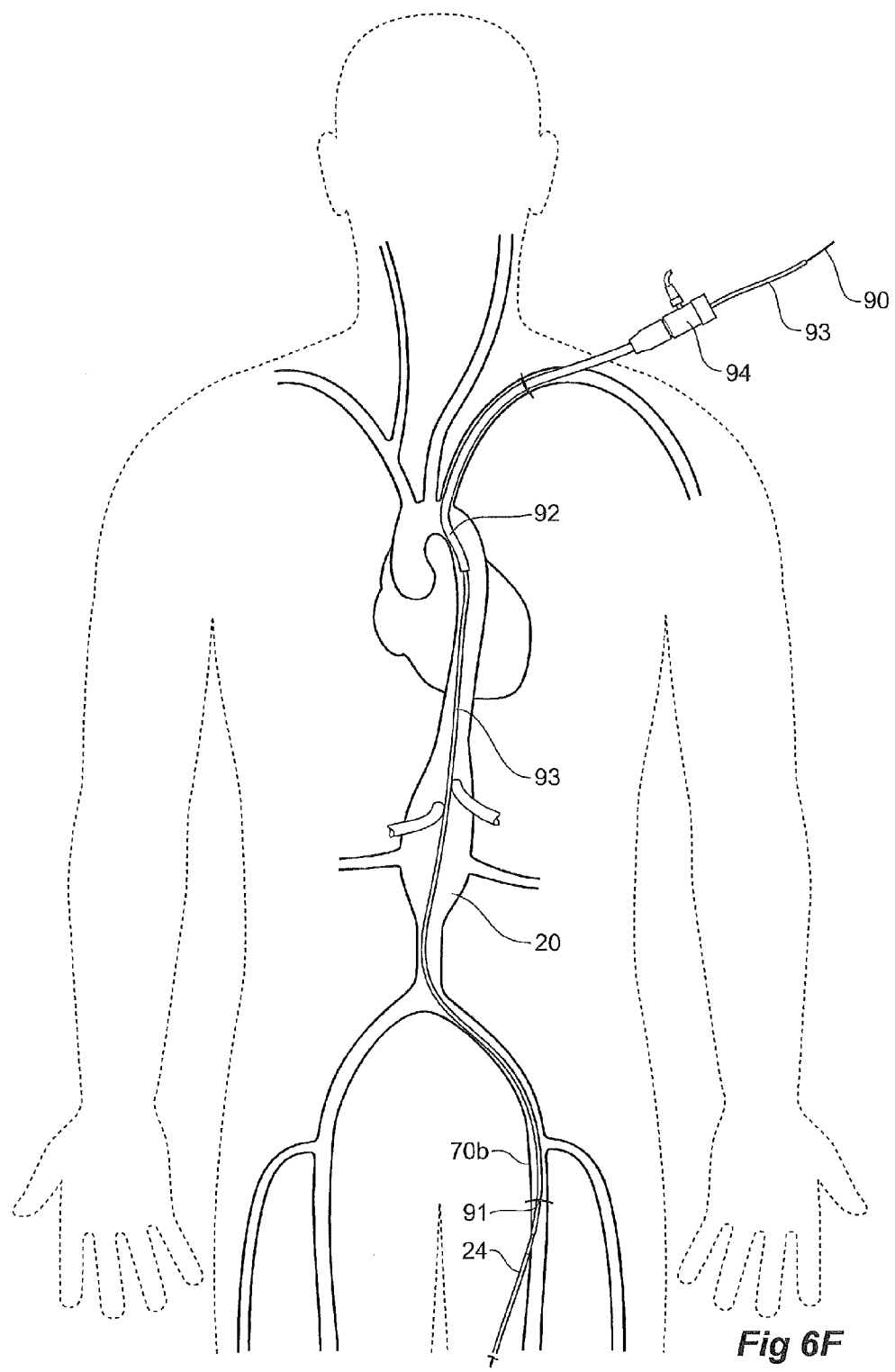
Figure 6G:
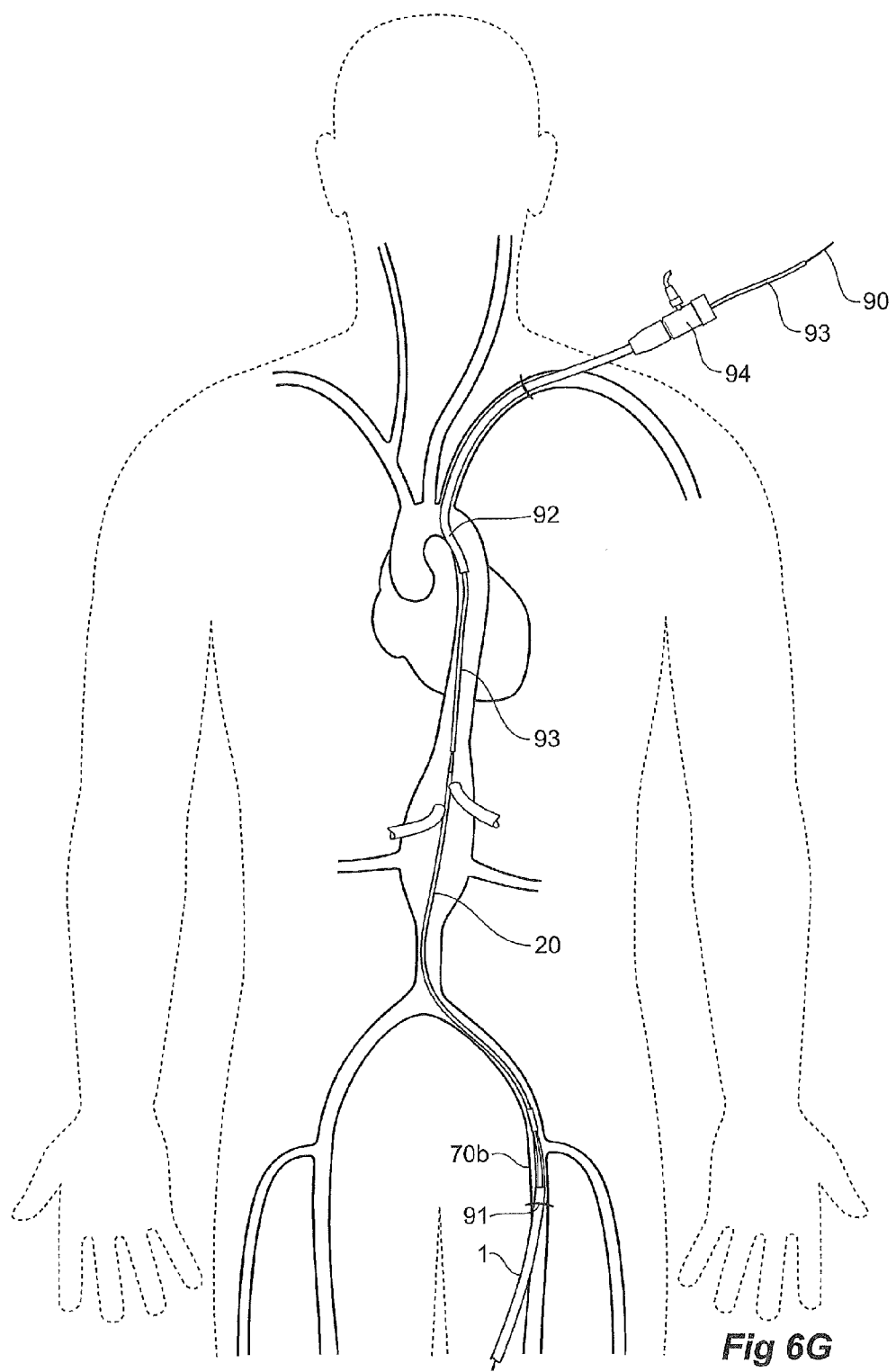
Figure 6H:
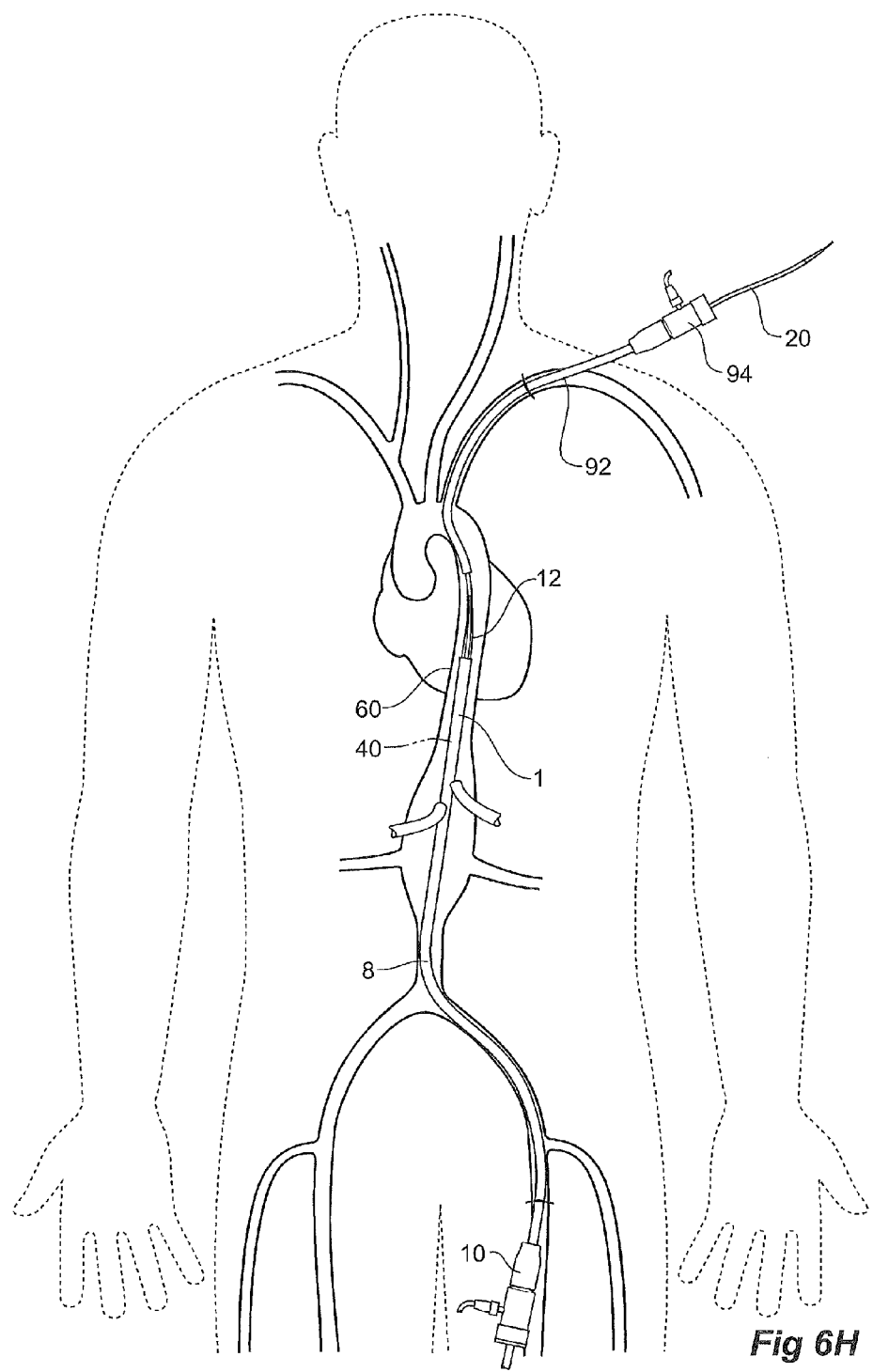
Figure 6I:
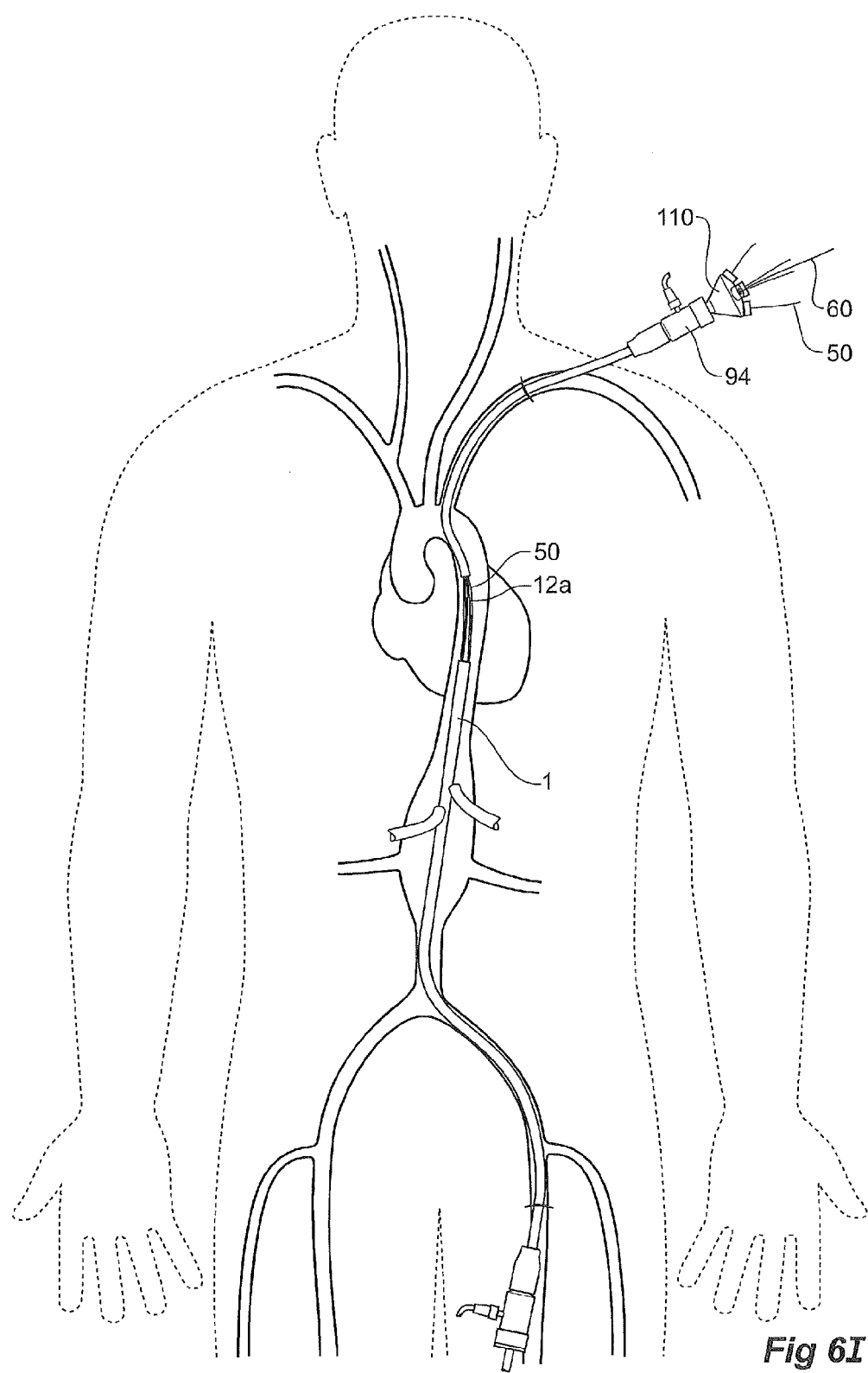
Figure 6J:
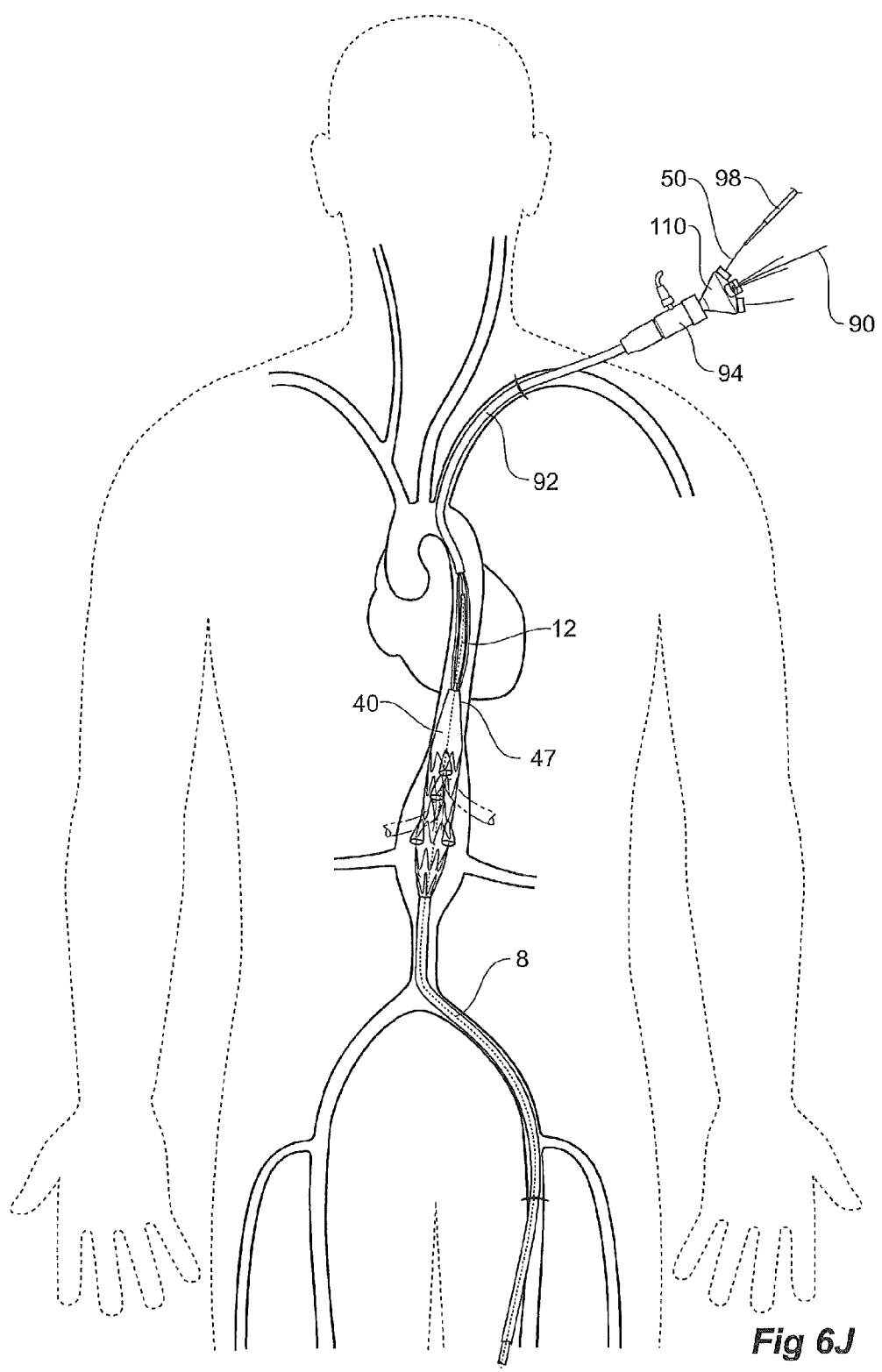
Figure 6K:
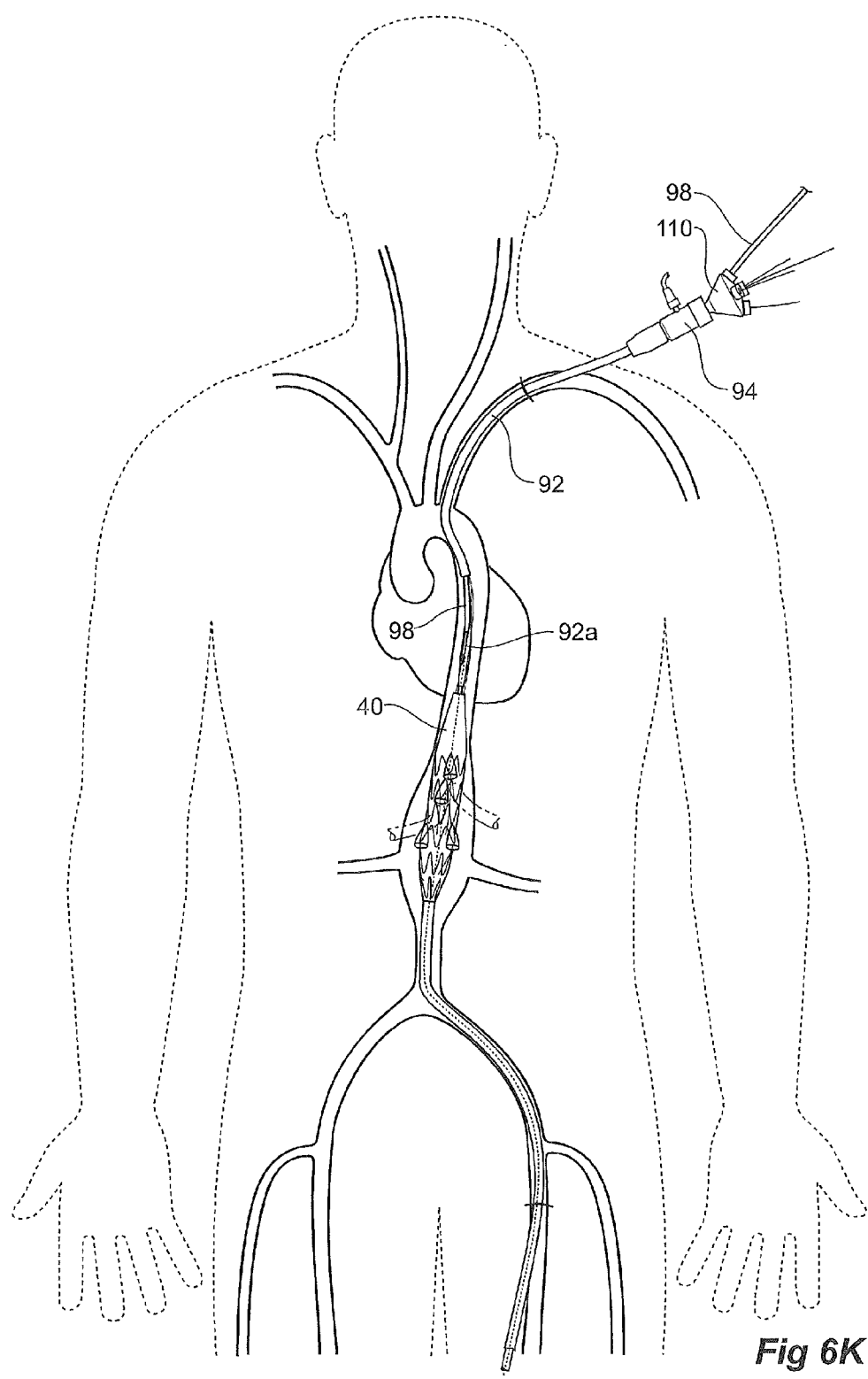
Figure 6L:
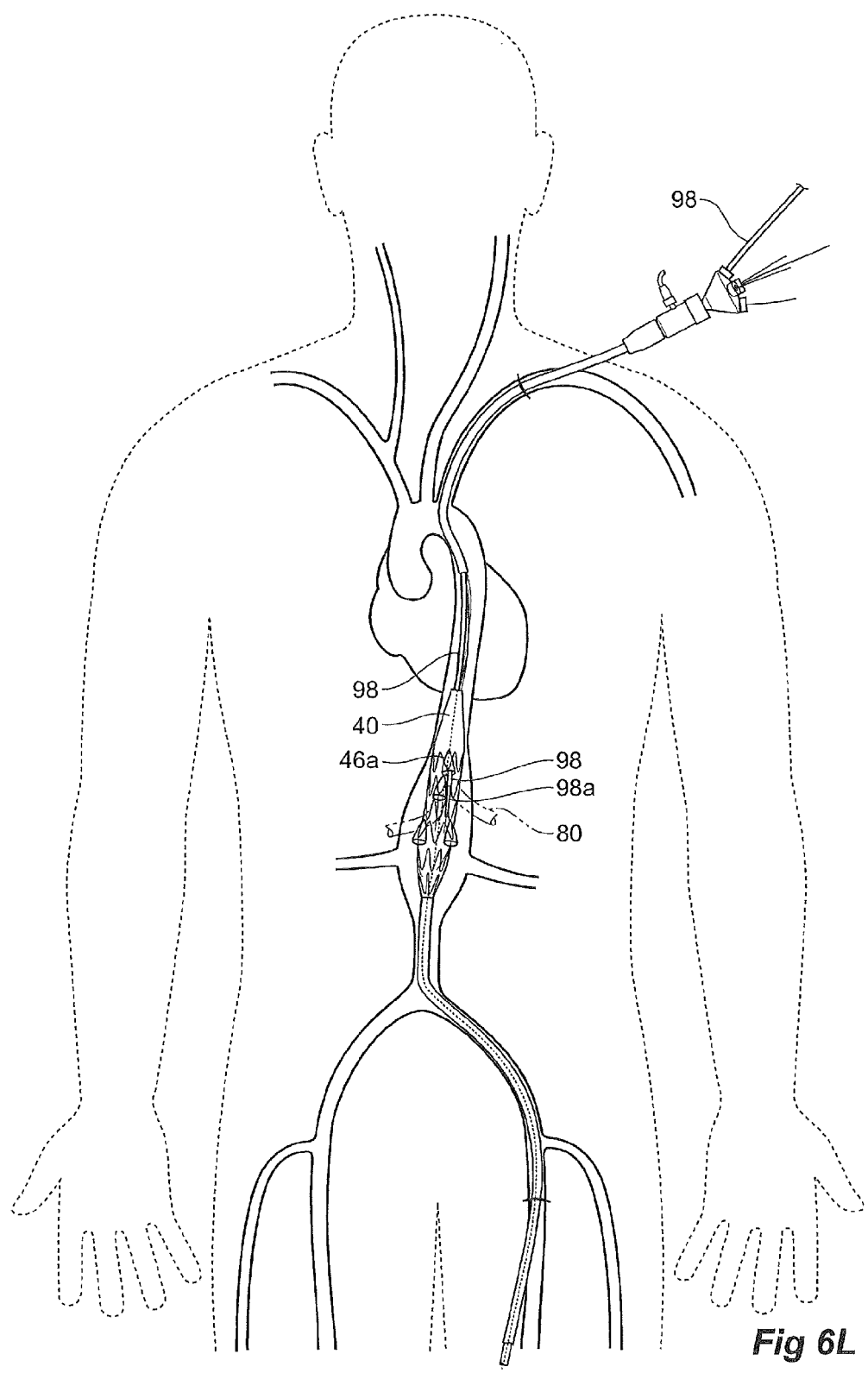
Figure 6M:
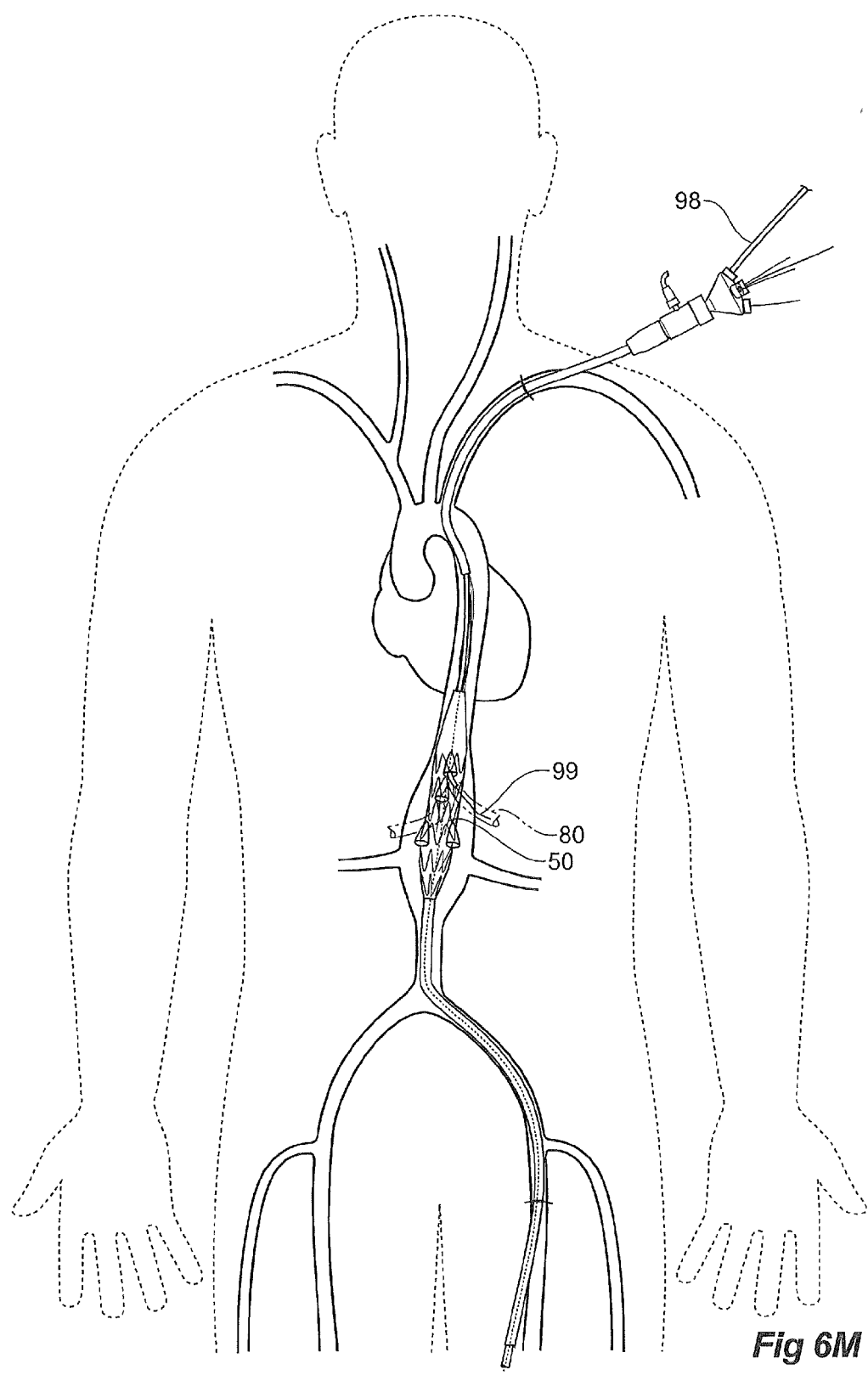
Figure 6N:
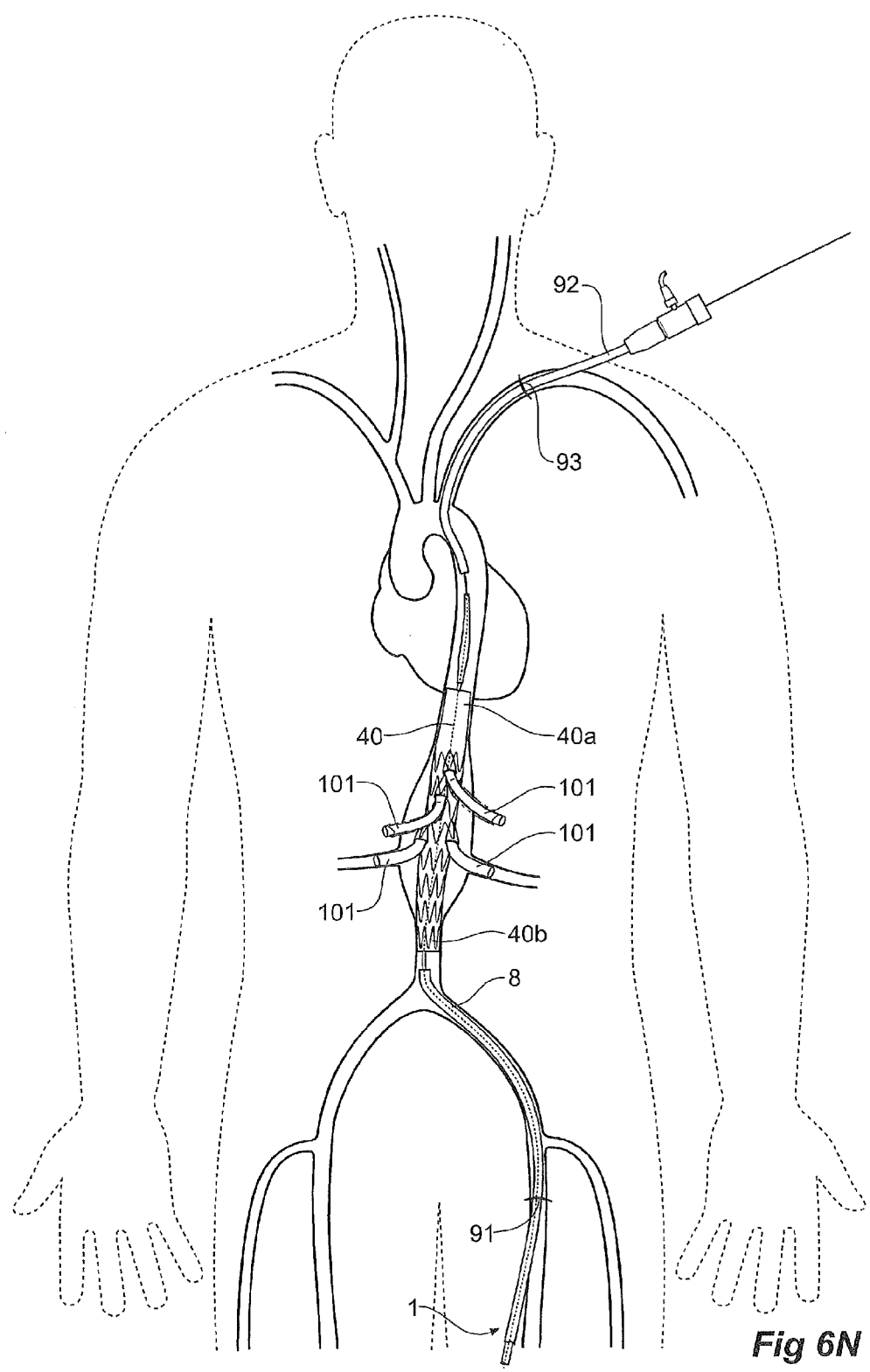

FIGS. 6A to 6N show various stages in the deployment of a stent graft using a delivery device according to the present invention.

FIGS. 6A to 6N show a schematic view of the vasculature of a human body. The vasculature shown comprises an aorta 60 extending from a heart 62 over a thoracic arch 64 to an aortic bifurcation 66. At the aortic bifurcation, iliac arteries 68*a* and 68*b* extend down to respective femoral arteries 70*a* and 70*b*. From the thoracic arch the brachiocephalic artery 72, the carotid artery 74 and the left subclavian artery 76 extend. In the aorta, there are renal arteries 77 and 78 extending from the aorta and little above them the superior mesenteric artery 79 and celiac artery 80. These four arteries can generally be referred to as the pararenal arteries. The aorta 60 is depicted with an aneurism 82 which has occurred in the region of the pararenal arteries and it is desired to deploy a stent graft into the aorta to span the aneurism while at the same time allowing catheterization and side arm deployment into the renal arteries, the superior mesenteric artery and the celiac artery.

In the first stage of the process as is shown in FIG. 6A, a guide wire 90 is introduced through a femoral puncture 91 into the femoral artery 70*a* and extended up through the femoral artery 70*a*, the iliac artery 68*b* and into the aorta 60 until it is just proximal of the pararenal arteries. A 12 French sheath 92 with sheath hub 94 is introduced via a brachial puncture in the left subclavian artery 76 and the sheath 92 extended down through the left subclavian artery into the descending aorta 60*a*.

As can be seen in FIG. 6B, a grasper device 96 with a snare 98 is introduced through the sheath hub 94 and down the sheath 92 until the snare 98 can engage the guide wire 90.

As can be seen in FIG. 6C, the snare 98 is used to draw the guide wire 90 back through the sheath 92 so that it extends out of the hub 94. This establishes a femoral to subclavian through and through wire.

In an alternative arrangement the grasper device with a snare can be introduced through a femoral artery puncture 91 and the guide wire can be introduced through the sheath hub 94 until the snare can engage the guide wire. The snare is then used to draw the guide wire back through the femoral puncture 91. This establishes a femoral to subclavian through and through wire.

As can be seen in FIG. 6D, a dilator 93 and catheter 95 is introduced through the hub 94 and tracked over the through and through guide wire 90 until it exits the femoral puncture 91 as shown in FIG. 6E. The dilator 95 is then removed leaving the catheter 93 in place.

As shown in FIG. 6F the proximal end of the extension dilator 26 of the deployment device 1 according to the present invention is introduced into the femoral artery 70*b* over the guide wire 90 and engaged with the catheter 93. This assembly is then deployed through the femoral puncture 91. The catheter 93, the elongate extension 20 of the introduction device 1 track over the guide wire 90 as shown in FIG. 6G.

This is continued until the catheter 93 is completely withdrawn and the extension catheter 24 and extension dilator extend into the sheath 92 and out through the hub 94 as is shown in FIG. 6H. At this stage, the nose cone dilator 12 of the introduction device is in such a position in the aorta 60 that the stent graft retained within the sheath 8 is in proximity to its desired final position.

In the next stage as is shown in FIG. 6I, auxiliary guide wires 50 are released from the handle portion of the delivery device 1 so that auxiliary guide wires 50 can be separated from the elongate extension piece 20 and if necessary cut to give four separate auxiliary guide wires. The elongate extension piece 20 can then be removed from its selective engagement with the proximal end 12*a* of the nose cone dilator 12. The elongate extension piece is removed from its selective engagement with the proximal end 12*a* of the nose cone dilator 12 by giving it a sharp pull where it extends out of the hub 94 and the elongate extension piece is removed through the hub 94 of the sheath 92 such that the auxiliary guide wires 50 remain in place and extend out through the hub 94. At this stage an adaptor piece 110 (see FIGS. 7 and 8) has the four auxiliary wires 50 and the main guide wire deployed into its seals and the adaptor piece is fitted into the hub 94 (see detail in FIG. 8).

The auxiliary guide wires 50 are then essentially through-and-through guide wires along with the main guide wire 90. The guide wires 50 can be marked at their distal ends where they extend from the handle of the introduction device (see FIG. 1) and by individual movement of each wire it can be determined which wire extends through which of the side arms of the stent graft. Alternatively the guide wire can be color coded so that an physician knows which auxiliary guide extends through which of the low profile side arms in the stent graft.

In the next stage as shown in FIG. 6J, the sheath hub 10 is retracted to withdraw the sheath 8 from the stent graft 40 so that the stent graft 40 is at least partially exposed but the proximal end 47 is still retained by means not shown just distal of the nose cone dilator 12.

A 7 French vessel access sheath 98 can then be advanced over one of the auxiliary guide wires 50 through the adaptor piece 110 into the hub 94 and through the sheath 92 to exit from the distal end 92a of the sheath 92 and to extend into the interior of the stent graft 40 through the open end as discussed in relation to FIG. 1B and out through the distal opening of one of the low profile side arms 46a. This stage is shown in FIG. 6K.

At this stage, the auxiliary guide wire 50 still extends through the material of the stent graft distal of the low profile side arm. The dilator 98a of the vessel access sheath 98 can then be retracted from the brachial end of the arrangement and a further guide wire 99 introduced to catheterize the celiac artery 80 (for instance) as is shown in FIG. 6M. The auxiliary guide wire 50 which still extends through the material of the stent graft distal of the low profile side arm assists in stabilizing the vessel access sheath 98 where it extends from the low profile side arm.

Standard catheter and wire techniques can then be used to manipulate the catheter and stiff wire into the selected target vessel to deploy side arms and/or covered bridging stents 101 into each of the pararenal vessels as is shown in FIG. 6N.

As each side arm is deployed the respective auxiliary guide wire 50 can be removed.

The sheath 8 can then be retracted to release the distal end 40b of the stent graft 40 and the proximal retention mechanisms can be activated to release the proximal end 47 to fully deploy the stent graft 40. The introduction device 1 can then be retracted through the femoral puncture 91 and the access sheath 92 retracted through the brachial puncture 93.

FIGS. 7A to 7D show alternative embodiments of adaptor pieces used to help preventing tangling and to facilitate placement of catheters over the auxiliary guide wires. FIG. 7A shows one embodiment of a manifold adaptor piece for use with the present invention and FIGS. 7B and 7C show an alternative embodiment of a manifold adaptor piece for use with the present invention and FIG. 7D shows a still further embodiment. FIG. 8 shows the use of the manifold adaptor piece shown in FIG. 7B.

In FIG. 7A a longitudinal cross sectional view of a manifold adaptor piece is shown. The adaptor piece 120 has a spigot 122 which is adapted to engage into the haemostatic seal of an endovascular port hub 94 as that shown in FIGS. 6H to N. The spigot has a annular recess 123 which acts to engage the haemostatic seal 94a of the hub 94. The adaptor piece 120 has a flared body 124 and a large seal disc 126 through which guide wires can be extended in a sealing manner. The adaptor piece in this embodiment essentially provides a larger area sealing surface than that of the hub 94 through which the various guide wires can be extended and be sealed around and which will prevent loss of blood through inadequate sealing due to crowding of the seal. The seal disc can be made from silicone or a similar material.

FIGS. 7B and 7C show an alternative embodiment of a manifold adaptor piece. In this embodiment the adaptor piece 130 has a spigot 132 which is adapted to engage into the haemostatic seal of an endovascular port hub 94 as that shown in FIGS. 6H to N. The adaptor piece 130 has a flared body 134 and a number of individual ports 136 each of which is provided with a seal disc 138.

In the embodiment shown in FIG. 7D the adaptor piece 140 has a spigot 122 which is adapted to engage into the haemostatic seal of an endovascular port hub 94 as that shown in FIGS. 6H to N. The spigot has a substantially cylindrical body which is longer than the spigot in the other embodiments discussed above and can be retained in the haemostatic seal 94a of the hub 94 by being pushed further in. The adaptor piece 140 has a flared body 144 and a number of individual ports 146 each of which is provided with a seal disc through which guide wires can be extended in a sealing manner.

In use as shown in FIG. 8 the spigot 132 of the adaptor piece 130 shown in FIGS. 7B and C is engaged into the haemostatic seal 94a of the endovascular port hub 94 and the guide wires 90 and 50 extend through the hub and a selected one of the individual ports 136 through its respective seal 138.

The manifold adaptor piece of either embodiment can be supplied for use with a plurality of pre-placed catheters into which the main guide wire 90 and the auxiliary guide wires 50 can be placed before engaging the spigot 122, 132 into the haemostatic seal 94a. Alternatively a needle can be used to pierce the large seal 126 or the individual seals 138, the respective guide wire placed through the needles and the needle removed to leave the guide wires through the seal.

The invention claimed is:

1. A stent graft delivery device comprising;
an introducer portion, the introducer portion comprising a distal handle portion to remain outside a patient in use and a proximal portion, wherein the proximal introducer portion comprises a pusher catheter, a guide wire catheter within the pusher catheter, the guide wire catheter being movable with respect to the pusher catheter, a nose cone dilator at a proximal end of the guide wire catheter, the nose cone dilator comprising a plurality of longitudinal grooves on an outside surface thereof;
an elongated extension piece comprising an elongate extension sheath and an extension dilator in the extension sheath, the elongated extension piece extending from a proximal end of the nose cone dilator, the elongate extension piece being selectively separable from the introducer portion; and
a plurality of auxiliary guide wires extending from the introducer portion through the introducer portion and through the elongate extension piece, the plurality of longitudinal grooves on the nose cone configured to receive the respective plurality of auxiliary guide wires therealong,
whereby the stent graft delivery device can be introduced into a patient via a femoral artery and the elongated extension piece can extend out an artery of the thoracic arch whereby to extend the auxiliary guide wires out of such an artery.

2. A stent graft delivery device as in claim 1 wherein the extension dilator comprising a plurality of longitudinal apertures on an outside surface thereof and the plurality of auxiliary guide wires extending along respective longitudinal apertures.

3. A stent graft delivery device as in claim 1 wherein a stent graft is carried on the introducer portion and the stent graft comprises a tubular body, the tubular body comprising proximal and distal open ends and a plurality of fenestrations or side arms, each of the auxiliary guide wires extending through a respective fenestration or side arm, the auxiliary guide wires extending through the tubular body proximally of the respective fenestration or side arm and outside the tubular body distally of the respective fenestration or side arm.

4. A stent graft delivery device as in claim 1 wherein the plurality of longitudinal grooves on at least part of the outside surface of the nose cone dilator comprise a substantially closed tube except for a narrow elongated opening whereby the respective auxiliary guide wires are received and retained therein.

5. A stent graft delivery device as in claim 1 wherein the elongate extension piece is removably engaged with the proximal end of the nose cone by being a friction fit therewith.

6. A stent graft delivery device as in claim 1 wherein the elongate extension piece is removably engaged with the proximal end of the nose cone, the device further including a trigger wire release mechanism, whereby upon release of the trigger wire release mechanism the elongate extension piece can be removed from the proximal portion.

7. A stent graft delivery device as in claim 1 wherein the auxiliary guide wires extend through the introducer portion to the handle portion.

8. A stent graft delivery device as in claim 1 wherein the auxiliary guide wires include markers at either or both of their proximal or distal ends.

9. A stent graft delivery device as in claim 1 wherein the plurality of auxiliary guide wires comprise a first and a second continuous auxiliary guide wire, each continuous wire extending from the distal handle portion to a proximal end of the elongate extension piece and returning to the distal handle portion.

10. A stent graft delivery device as in claim 9 wherein the elongate extension piece comprises an elongate extension sheath and an extension dilator in the extension sheath and the extension dilator extending proximally of extension sheath, the extension dilator comprising a plurality of longitudinal apertures and the auxiliary guide wires extending through the longitudinal apertures, a pair of scallops extending into the extension dilator at the proximal end of the extension dilator between adjacent longitudinal apertures whereby the auxiliary wires cross over to return in an adjacent longitudinal aperture.

11. A stent graft delivery device as in claim 9 wherein the elongate extension piece comprises an elongate extension sheath and an extension dilator in the extension sheath and the extension dilator extending proximally of extension sheath, the extension dilator comprising a plurality of longitudinal grooves on an outside surface thereof and the plurality of auxiliary guide wires extending along respective longitudinal grooves, a pair of cross apertures extending into the extension dilator between adjacent longitudinal grooves at the proximal end of the extension dilator whereby each of the auxiliary guide wires cross through a respective cross aperture to return in an adjacent longitudinal groove.

12. A stent graft delivery device and stent graft in combination, the stent graft being loaded onto the delivery device;
the delivery device comprising an introducer portion comprising a distal handle portion to remain outside a patient in use and a proximal portion, wherein the proximal introducer portion comprises a pusher catheter, a guide wire catheter within the pusher catheter and a nose cone dilator comprising a plurality of longitudinal grooves on an outside surface thereof at a proximal end of the guide wire catheter and an elongate extension piece extending from a proximal end of the nose cone dilator; the elongate extension piece selectively separable from the introducer portion, and
a plurality of auxiliary guide wires extending from the distal end of the introducer portion through the introducer portion and through the elongate extension piece to a proximal end of the elongate extension piece, the elongate extension piece comprising an elongate extension sheath and an extension dilator in the extension sheath and extending proximally thereof, the extension dilator comprising a plurality of longitudinal grooves on an outside surface thereof;
the stent graft comprising a tubular body, the tubular body comprising proximal and distal open ends and a plurality of fenestrations or side arms, the stent graft being retained on the introducer portion distally of the nose cone dilator and proximally pusher catheter;
each of the auxiliary guide wires extending through a respective fenestration or side arm, the auxiliary guide wires extending through the tubular body proximally of the respective fenestration or side arm and outside the tubular body distally of the respective fenestration or side arm;
whereby the stent graft delivery device can be introduced into a patient via a femoral artery and the elongate extension piece can extend out a thoracic arch artery whereby to extend the auxiliary guide wires out of such an artery and the respective auxiliary guide wires can be used to catheterize the respective fenestration or side arm and subsequently to deploy an extension stent graft therethrough.

13. A stent graft delivery device and stent graft in combination as in claim 12 wherein the plurality of longitudinal grooves on at least part of the outside surface of the nose cone dilator comprise a substantially closed tube except for a narrow elongated opening.

14. A stent graft delivery device and stent graft in combination as in claim 12 wherein the elongate extension piece is removably engaged with the proximal end of the nose cone dilator by being a friction fit therewith or by including a trigger wire release mechanism, whereby upon release of the trigger wire release mechanism the elongate extension piece can be removed from the proximal end of the nose cone dilator.

15. A stent graft delivery device and stent graft in combination as in claim 14 wherein the elongate extension piece comprises an elongate extension sheath and an extension dilator in the extension sheath and the extension dilator extending proximally of extension sheath, the extension dilator comprising a plurality of longitudinal apertures or grooves and the auxiliary guide wires extending through the longitudinal apertures or grooves, cross over recesses extending into the extension dilator at the proximal end of the extension dilator between adjacent longitudinal apertures or grooves whereby the auxiliary wires cross in the cross over recesses to return in an adjacent longitudinal aperture or groove.

16. A stent graft delivery device and stent graft in combination as in claim 12 wherein the plurality of auxiliary guide wires comprise a first and a second continuous wire, each continuous wire extending from the distal handle portion to the proximal end of the elongate extension piece and returning to the distal handle portion.

17. A stent graft delivery device and stent graft in combination, the stent graft being loaded onto the delivery device;
the delivery device comprising an introducer portion comprising a distal handle portion to remain outside a patient in use and a proximal introduction portion
comprising a pusher catheter, a guide wire catheter within the pusher catheter, the guide wire catheter being movable with respect to the pusher catheter, a nose cone dilator at a proximal end of the guide wire catheter, the nose cone dilator comprising a plurality of longitudinal grooves on an outside surface thereof;
   an elongate extension piece extending from a proximal end of the nose cone dilator, the elongate extension piece comprising an elongate extension sheath and an extension dilator in the extension sheath and the extension dilator extending proximally of extension sheath, the extension dilator comprising a plurality of longitudinal apertures;
   a plurality of auxiliary guide wires extending from the distal end of the introducer portion through the pusher catheter, along the longitudinal grooves in the nose cone dilator, into and through the extension sheath through the longitudinal apertures on the extension dilator, a pair of scallops extending into the extension dilator at the proximal end of the extension dilator between adjacent longitudinal apertures whereby the auxiliary wires cross over to return in an adjacent longitudinal aperture;
   the plurality of auxiliary guide wires comprising a first and a second continuous wire, each continuous wire extending from the distal handle portion to the proximal end of the elongate extension piece and returning to the distal handle portion,
   the stent graft comprising a tubular body, the tubular body comprising proximal and distal open ends and a plurality of fenestrations;
   each of the auxiliary guide wires extending through a respective fenestration, the auxiliary guide wires extending through the tubular body proximally of the respective fenestration and outside the tubular body distally of the respective fenestration;
   whereby the stent graft delivery device can be introduced into a patient via a femoral artery and the elongated dilator extension can extend out of a thoracic arch artery whereby to extend the auxiliary guide wires out of the artery and subsequently to
cut the first and the second continuous wire where they extend out through the artery to give four auxiliary guide wires and then to deploy side arm extension along the respective guide wires into the respective fenestrations.

18. A stent graft delivery device and stent graft in combination as in claim 17 wherein the elongate extension piece is removably engaged with the nose cone dilator by being a friction fit therewith.

19. A stent graft delivery device and stent graft in combination as in claim 17 wherein the elongate extension piece is removably engaged with the nose cone dilator and including a trigger wire release mechanism, whereby upon release of the trigger wire release mechanism, operable from the distal handle portion, the elongate extension piece can be separated from the nose cone dilator.

* * * * *